US009968659B2

(12) United States Patent
Rasmussen

(10) Patent No.: US 9,968,659 B2
(45) Date of Patent: May 15, 2018

(54) LIRAGLUTIDE IN CARDIOVASCULAR CONDITIONS

(71) Applicant: Novo Nordisk A/S, Bagsvaerd (DK)

(72) Inventor: Soeren Rasmussen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days. days.

(21) Appl. No.: 15/401,651

(22) Filed: Jan. 9, 2017

(65) Prior Publication Data

US 2017/0252408 A1  Sep. 7, 2017

(30) Foreign Application Priority Data

Mar. 4, 2016 (EP) .................................... 16158739
Jun. 10, 2016 (EP) .................................... 16173917
Jun. 13, 2016 (EP) .................................... 16001329

(51) Int. Cl.
A61K 38/26  (2006.01)
A61P 3/10  (2006.01)
A61P 7/12  (2006.01)
C07K 14/605  (2006.01)

(52) U.S. Cl.
CPC .................................. A61K 38/26 (2013.01)

(58) Field of Classification Search
CPC ..... A61K 38/26; A61K 38/2278; A61K 38/00
See application file for complete search history.

(56) References Cited

U.S. PATENT DOCUMENTS

| 5,808,203 A | 9/1998 | Nolan, Jr. et al. |
| 2003/0220255 A1 | 11/2003 | Knudsen et al. |
| 2010/0256153 A1 | 10/2010 | Frederich et al. |

FOREIGN PATENT DOCUMENTS

| WO | 10015664 A1 | 2/2010 |
| WO | 10079197 A1 | 7/2010 |
| WO | 10086411 A1 | 8/2010 |
| WO | 2011140176 A1 | 11/2011 |
| WO | 11161161 A1 | 12/2011 |
| WO | 12065993 A1 | 5/2012 |
| WO | 13098372 A1 | 7/2013 |
| WO | 13171166 A1 | 11/2013 |
| WO | 13171167 A1 | 11/2013 |
| WO | 13174768 A1 | 11/2013 |
| WO | 14140284 A1 | 9/2014 |
| WO | 14198906 A1 | 12/2014 |
| WO | 15085044 A1 | 6/2015 |
| WO | 15128453 A1 | 9/2015 |
| WO | 16019587 A1 | 2/2016 |

OTHER PUBLICATIONS

Fleiss et al., Circulation, 1990, 81, 684-685.*
Konzem et al., American Family Physician, 2002, 66, 7, 1209.*
Frost et al., Expert Opin. Pharmacother., 2012, 13(1):101-110.*
van der Elst et al., The Annals of Pharmacotherapy, 2003, vol. 37, 1465.*
Briyal S et al "Neuroprotective and anti-apoptotic effects of liraglutide in the rat brain following focal cerebral ischemia" Neuroscience, 2014, vol. 281, pp. 269-281.
Gejl et al., Risk of cardiovascular disease: The effects of diabetes and anti-diabetic drugs—A nested case-control study, International Journal of Cardiology, 2015, vol. 178, pp. 292-296.
James P Smith "Saxenda (liraglutide [rDNA origin] injection), solution for subcutaneous use" Internet Citation Dec. 23, 2014, XP002760221, Retrieved from the Internet: URL: http://www.accessdata.fda.gov/drugsatfda_docs/label/2014/206321orig1s000lbl.pdf [retrieved on Sep. 15, 2016].
M.H. Noyan-Ashraf et al "GLP-1R Agonist Liraglutide Activates Cytoprotective Pathways and Improves Outcomes After Experimental Myocardial Infarction in Mice" Diabetes, 2009, vol. 58, No. 4, pp. 975-983.
Manfredi Rizzo et al "Liraglutide Reduces Oxidative Strees and Restores Heme Oxygenase-1 and Ghrelin Levels in Patients with Type 2 Diabetes: A Prospective Pilot Study" Journal of Clinical Endocrinology and Metabolism, 2015, vol. 100, No. 2, pp. 603-606.
Marso et al., Cardiovascular safety of liraglutide in a patient-level pooled analysis of phase 2-3 liraglutide clinical development studies, Diabetes & Vascular Disease Research, 2011, vol. 8, No. 3, pp. 237-240.
Marso et al., Design of the liraglutide effect and action in diabetes: Evaluation of cardiovascular outcome results, American Heart Journal, 2013, vol. 166, No. 5, pp. 823-830.
Monami et al., Effects of glucagon-like peptide-1 receptor agonists on cardiovascular risk: a meta-analysis of randomized clinical trials, Diabetes, Obesity and Metabolism, 2014, vol. 16, pp. 38-47.
Mundil Dhanwantee et al "GLP-1 receptor agonists: a clinical perspective on cardiovascular effects" Diabetes & Vascular Disease Research, 2012, vol. 9, No. 2 pp. 95-108.
Raymond T et al. "Management of patient with diabetes and coronary artery disease: a contemporary review" Future Cardiology, Future Medicine LTD, 2013, vol. 9, No. 3, pp. 387-403.
Rotz et al., Implications of incretin-based therapies on cardiovascular disease, International Journal of Clinical Practice, 2015, vol. 69, No. 5, pp. 531-549.
Scheel-Thomsen et al "Diabetes and Stroke: Liraglutide is associated with a decrease risk of stroke in type 2 diabetes mellitus. A Nested case-control study" European Journal of Nuerology 2014 vol. 21 No. Suppl 1 p. 154.
Steven P. Marso et al "Liraglutide and Cardiovascular Outcomes in Type 2 Diabetes" New England Journal of Medicine, 2016, vol. 375, No. 4, pp. 311-322.
Verge D et al. "Impact of GLP-1 and GLP-1 receptor agonists on cardiovascular risk factors in type 2 diabetes" Current Diabetes Reviews, 2010, vol. 6, No. 4, pp. 191-200.
Verges et al., Beyond glucose lowering: Glucagon-like peptide-1 receptor agonists, body weight and the cardiovascular system, Diabetes & Metabolism, 2011, vol. 37, pp. 477-488.

(Continued)

*Primary Examiner* — Hasan S Ahmed
*Assistant Examiner* — Kaipeen E Yang
(74) *Attorney, Agent, or Firm* — Leon Y. Lum

(57) ABSTRACT

The present invention relates to the GLP-1 receptor agonist liraglutide for use in medicine.

18 Claims, 7 Drawing Sheets

(56) References Cited

OTHER PUBLICATIONS

Wu Jing et al "Long term health outcomes of liraglutide combined with metformin in type 2 diabetes patients: an analysis using CORE diabetes model" Zhongguo Xinyao Yu Linchuang Zazhi, 2011, vol. 30 ,No. 6, pp. 422-427; Databse Biosis [Online] Biosciences Information Service, Philadelphia PA, Jun. 2011, XP002760353 Database Accession No. PREV201100516436.
Zavattaro Marco et al "One-year treatment with liraglutide improved renal function in patients with type 2 diabetes: a pilot prospective study" Endocrine, 2015, vol. 50, No. 3, pp. 620-626.
Kip et al., "The Problem With Composite End Points in Cardiovascular Studies the Story of Major Adverse Cardiac Events and Percutaneous Coronary Intervention," Journal of the American College of Cardiology, 2008, vol. 51, No. 7, pp. 701-707.

* cited by examiner

LIRAGLUTIDE IN CARDIOVASCULAR CONDITIONS

The present invention relates to the GLP-1 receptor agonist liraglutide for use in cardiovascular conditions in a subject having at least diabetes.

CROSS-REFERENCE TO RELATED APPLICATIONS

This application claims priority under 35 U.S.C. § 119 to European Patent Application 16158739.9, filed Mar. 4, 2016, European Patent Application 16173917.2, filed Jun. 10, 2016, and European Patent Application 16001329.8, filed Jun. 13, 2016; the contents of which are incorporated herein by reference.

BACKGROUND

Diabetes is a metabolic disorder characterized by hyperglycaemia that is associated with a high risk of cardiovascular and other serious health-related consequences. A person with diabetes is two to three times more likely to die from cardiovascular causes than people with no history of diabetes, even after controlling for other cardiovascular risk factors. They are also at very high risk of developing serious microvascular complications ultimately leading to premature death: nephropathy and renal failure, retinal disease and blindness, autonomic and peripheral neuropathy, as well as other conditions related to the vascular system: hypertension, lower limb amputation, cognitive decline, and erectile dysfunction.

The majority of people with diabetes have type 2 diabetes, which is characterised by insulin resistance and eventually impaired insulin secretion. Optimal glycaemic control is the treatment goal in subjects with type 2 diabetes, since the risk of long-term complications is increased with poor glycaemic control. Despite the availability of several oral anti-diabetic drugs and insulin, a significant proportion of subjects with type 2 diabetes do not achieve the recommended target levels. With the increasing incidence and prevalence of type 2 diabetes, there is an unmet medical need for treatment alternatives with improved efficacy, safety and convenience.

SUMMARY

In some embodiments the present invention relates to a method of treating type 2 diabetes, comprising administering liraglutide in a therapeutically effective amount to a subject in need thereof, wherein said subject has (i) one or more vascular diseases selected from the group consisting of cardiovascular disease, cerebrovascular disease, peripheral vascular disease, chronic renal failure, and chronic heart failure, and/or (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9; wherein said method delays or reduces development of a major adverse cardiovascular event (MACE).

BRIEF DESCRIPTION OF DRAWINGS

FIG. 1-7 show the number of subjects at risk for the relevant event(s) at different time points after randomisation and are Kaplan-Meier plot of time to event.

DESCRIPTION

Figure 1:
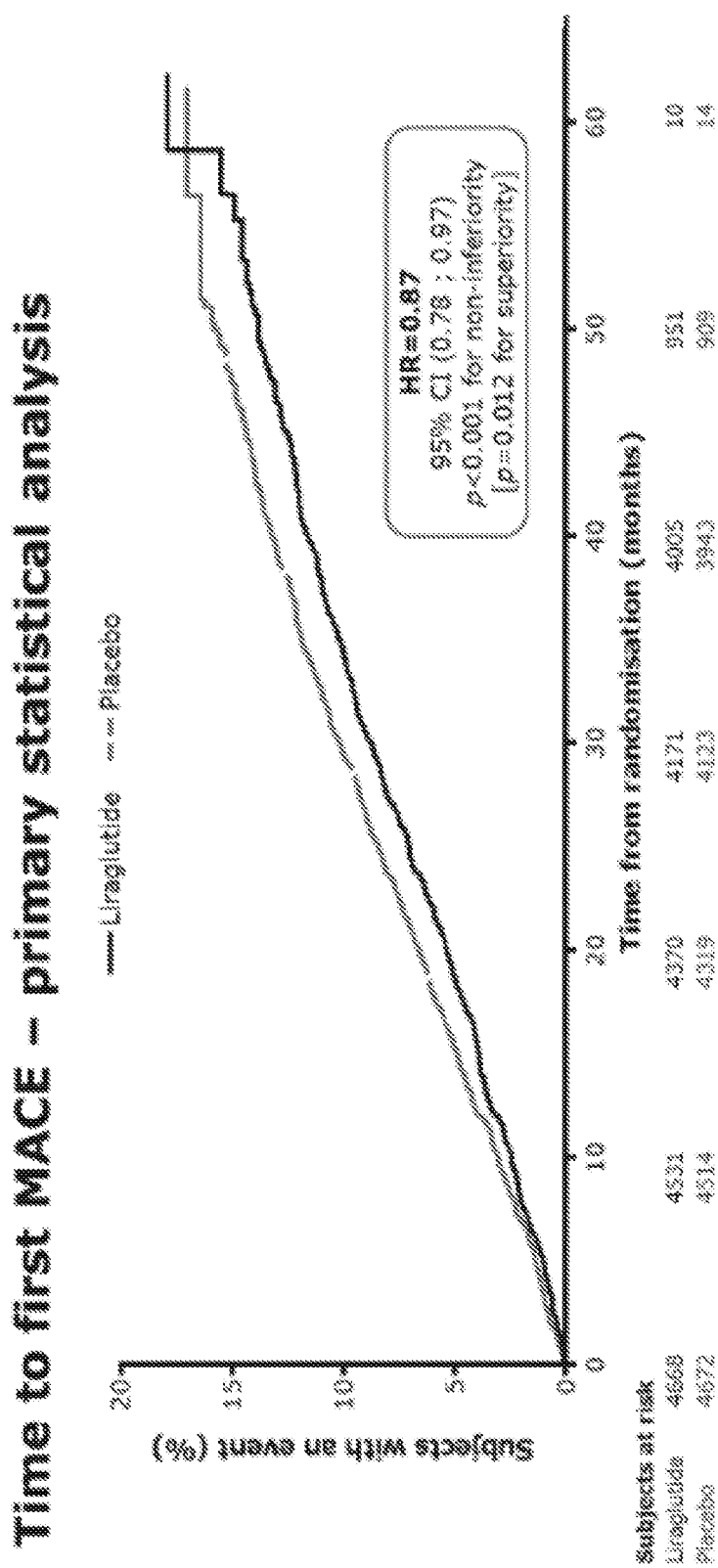
FIG. 1 shows time to first MACE selected from the group consisting of CV death, non-fatal MI, and non-fatal stroke following administration of liraglutide or its placebo.

In some embodiments the present invention relates to a method of treating type 2 diabetes, comprising administering liraglutide in a therapeutically effective amount to a subject in need thereof, wherein said subject has (i) one or more vascular diseases selected from the group consisting of cardiovascular disease, cerebrovascular disease, peripheral vascular disease, chronic renal failure, and chronic heart failure, and/or (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9; wherein said method reduces or delays a major adverse cardiovascular event (MACE).

The term "MACE" as used herein refers to major adverse cardiovascular event. In some embodiments MACE is events selected from the group consisting of cardiovascular (CV) death, non-fatal MI, non-fatal stroke, coronary revascularisation, hospitalisation for unstable angina pectoris, and hospitalisation for chronic heart failure. In some embodiments MACE is CV death. In some embodiments MACE is non-fatal MI. The term "non-fatal MI" as used herein refers to non-fatal myocardial infarction. In some embodiments MACE is events selected from the group consisting of CV death, non-fatal MI, and non-fatal stroke. In some embodiments MACE is non-fatal stroke. In some embodiments MACE is coronary revascularisation. In some embodiments MACE is hospitalisation for unstable angina pectoris. In some embodiments MACE is hospitalisation for chronic heart failure.

In some embodiments the present invention relates to a method of treating type 2 diabetes, comprising administering liraglutide in a therapeutically effective amount to a subject in need thereof, wherein said subject has vascular disease and/or one or more risk factors of vascular disease. In some embodiments the vascular disease is selected from the group consisting of cardiovascular disease, cerebrovascular disease, peripheral vascular disease, chronic renal failure, and chronic heart failure. In some embodiments the subject has (i) vascular disease selected from the group consisting of cardiovascular disease, cerebrovascular disease, peripheral vascular disease, chronic renal failure, and chronic heart failure. In some embodiments the subject has (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9. In some embodiments the vascular disease and/or said one or more risk factors of vascular disease was present before initiation of liraglutide administration.

In some embodiments the method reduces or delays a major adverse cardiovascular event (MACE). In some embodiments the method reduces the risk of said subject developing a major adverse cardiovascular event (MACE). In some embodiments the method reduces the risk of said subject developing its first MACE. The term "first MACE" as used herein refers to the first MACE event of a subject after initiation of liraglutide administration.

In some embodiments the one or more risk factors of vascular disease are selected from the group consisting of a) microalbuminuria or proteinuria; b) hypertension and/or left ventricular hypertrophy by ECG or imaging; c) left ventricular systolic or diastolic dysfunction by imaging; and d) ankle/brachial index <0.9. In some embodiments the risk factor of vascular disease is microalbuminuria. In some embodiments the risk factor of vascular disease is proteinuria. In some embodiments the risk factor of vascular disease is hypertension and left ventricular hypertrophy. In some embodiments the risk factor of vascular disease is left ventricular systolic dysfunction. In some embodiments the risk factor of vascular disease is left ventricular diastolic dysfunction. In some embodiments the risk factor of vascular disease is ankle/brachial index <0.9.

In some embodiments MACE is selected from the group consisting of CV death, non-fatal MI, non-fatal stroke, coronary revascularisation, hospitalisation for heart failure, and hospitalisation for unstable angina pectoris. In some embodiments the MACE is reduced or delayed by at least 1% compared to placebo. In some embodiments the MACE is reduced or delayed by from about 1% to about 3% compared to placebo. In some embodiments the MACE is reduced about 2.4% compared to placebo. In some embodiments the first MACE is reduced or delayed by at least 1% compared to placebo. In some embodiments the first MACE is reduced or delayed by from about 1% to about 3% compared to placebo. In some embodiments the first MACE is reduced about 2.4% compared to placebo.

In some embodiments MACE is selected from the group consisting of CV death, non-fatal MI, non-fatal stroke, coronary revascularisation, and hospitalisation for heart failure. In some embodiments MACE is selected from the group consisting of CV death, non-fatal MI, and non-fatal stroke. In some embodiments MACE is reduced or delayed by at least 10% compared to placebo. In some embodiments MACE is reduced or delayed by from about 10% to about 15% compared to placebo. In some embodiments MACE is reduced or delayed about 13% compared to placebo. In some embodiments MACE has a hazard ratio of about 0.87 compared to placebo. In some embodiments MACE has a hazard ratio of 0.87 with a 95% CI of (0.78; 0.97) compared to placebo. In some embodiments the risk of said subject developing a MACE is reduced by at least 10% compared to placebo. In some embodiments the risk of said subject developing a MACE is reduced by from about 10% to about 15% compared to placebo. In some embodiments the risk of said subject developing a MACE is reduced about 13% compared to placebo. In some embodiments the subject developing a MACE has a hazard ratio of about 0.87 compared to placebo. In some embodiments the subject developing a MACE has a hazard ratio of 0.87 with a 95% CI of (0.78; 0.97) compared to placebo. In some embodiments the subject developing its first MACE is reduced or delayed by at least 10% compared to placebo. In some embodiments the MACE is reduced or delayed by from about 10% to about 15% compared to placebo. In some embodiments the first MACE is reduced or delayed about 13% compared to placebo. In some embodiments the subject developing its first MACE has a hazard ratio of about 0.87 compared to placebo. In some embodiments the subject developing its first MACE has a hazard ratio of 0.87 with a 95% CI of (0.78; 0.97) compared to placebo.

In some embodiments the MACE is CV death. In some embodiments the CV death is reduced by at least 10% compared to placebo. In some embodiments the CV death is reduced or delayed by from about 10% to about 35% compared to placebo. In some embodiments the CV death is reduced or delayed by from about 15% to about 30% compared to placebo. In some embodiments the CV death is reduced or delayed by about 22% compared to placebo.

In some embodiments the MACE is non-fatal MI. In some embodiments the non-fatal MI is reduced or delayed by at least 8% compared to placebo. In some embodiments the non-fatal MI is reduced or delayed by from about 8% to about 20% compared to placebo. In some embodiments the non-fatal MI is reduced or delayed by from about 10% to about 15% compared to placebo. In some embodiments the non-fatal MI is reduced or delayed by about 12% compared to placebo.

In some embodiments the MACE is non-fatal stroke. In some embodiments the non-fatal stroke is reduced or delayed by at least 7% compared to placebo. In some embodiments the non-fatal stroke is reduced or delayed by from about 8% to about 20% compared to placebo. In some embodiments the non-fatal stroke is reduced or delayed by from about 9% to about 15% compared to placebo. In some embodiments the non-fatal stroke is reduced or delayed by about 11% compared to placebo.

In some embodiments the MACE is coronary revascularisation. In some embodiments the coronary revascularisation is reduced or delayed by at least 5% compared to placebo. In some embodiments the coronary revascularisation is reduced or delayed by from about 5% to about 20% compared to placebo. In some embodiments the coronary revascularisation is reduced or delayed by from about 7% to about 15% compared to placebo. In some embodiments the coronary revascularisation is reduced or delayed by about 9% compared to placebo.

In some embodiments the MACE is hospitalisation for heart failure. In some embodiments the hospitalisation for heart failure is reduced or delayed by at least 5% compared to placebo. In some embodiments the hospitalisation for heart failure is reduced or delayed by from about 8% to about 20% compared to placebo. In some embodiments the hospitalisation for heart failure is reduced or delayed by about 13% compared to placebo. In some embodiments the hospitalisation for heart failure is reduced or delayed by at least 10% compared to placebo. In some embodiments the hospitalisation for heart failure is reduced or delayed by from about 10% to about 35% compared to placebo. In some embodiments the hospitalisation for heart failure is reduced or delayed by from about 15% to about 30% compared to placebo. In some embodiments the hospitalisation for heart failure is reduced or delayed by about 23% compared to placebo.

In some embodiments the MACE is hospitalisation for unstable angina pectoris. In some embodiments the hospitalisation for unstable angina pectoris is reduced or delayed by at least 1% compared to placebo. In some embodiments the hospitalisation for unstable angina pectoris is reduced or delayed by from about 1% to about 5% compared to placebo. In some embodiments the hospitalisation for unstable angina pectoris is reduced or delayed by about 2% compared to placebo.

In some embodiments the MACE is a) CV death, and wherein said CV death is reduced or delayed by from about 10% to about 35% compared to placebo; b) non-fatal MI, and wherein said non-fatal MI is reduced or delayed by from about 8% to about 20% compared to placebo; c) non-fatal stroke, and wherein said non-fatal stroke is reduced or delayed by from about 8% to about 20% compared to placebo; and/or d) hospitalisation for heart failure, and wherein said hospitalisation for heart failure is reduced or delayed by from about 5% to about 20% compared to placebo. In some embodiments the MACE is a) CV death, and wherein said CV death is reduced or delayed by from about 10% to about 35% compared to placebo; b) non-fatal MI, and wherein said non-fatal MI is reduced or delayed by from about 8% to about 20% compared to placebo; c) non-fatal stroke, and wherein said non-fatal stroke is reduced or delayed by from about 8% to about 20% compared to placebo; and/or d) hospitalisation for heart failure, and wherein said hospitalisation for heart failure is reduced or delayed by from about 10% to about 35% compared to placebo. In some embodiments the MACE is CV death, and wherein said CV death is reduced or delayed by from about 10% to about 35% compared to placebo. In some embodiments the MACE is non-fatal MI, and wherein said non-fatal MI is reduced or delayed by from about 8% to about 20% compared to placebo. In some embodiments the MACE is non-fatal stroke, and wherein said non-fatal stroke is reduced or delayed by from about 8% to about 20% compared to placebo. In some embodiments MACE is hospitalisation for heart failure, and wherein said hospitalisation for heart failure is reduced or delayed by from about 5% to about 20% compared to placebo. In some embodiments MACE is hospitalisation for heart failure, and wherein said hospitalisation for heart failure is reduced or delayed by from about 10% to about 35% compared to placebo. In some embodiments MACE is a) CV death, and wherein said CV death is reduced or delayed by about 22% compared to placebo; b) non-fatal MI, and wherein said non-fatal MI is reduced or delayed by about 12% compared to placebo; c) non-fatal stroke, and wherein said non-fatal stroke is reduced or delayed by about 11% compared to placebo; and/or d) hospitalisation for heart failure, and wherein said hospitalisation for heart failure is reduced or delayed by about 13% compared to placebo. In some embodiments MACE is a) CV death, and wherein said CV death is reduced or delayed by about 22% compared to placebo; b) non-fatal MI, and wherein said non-fatal MI is reduced or delayed by about 12% compared to placebo; c) non-fatal stroke, and wherein said non-fatal stroke is reduced or delayed by about 11% compared to placebo; and/or d) hospitalisation for heart failure, and wherein said hospitalisation for heart failure is reduced or delayed by about 23% compared to placebo.

In some embodiments the method further reduces the risk of death of said subject, wherein the cause of said death is any cause. In some embodiments the risk of death of said subject is reduced by at least 10% compared to placebo. In some embodiments the risk of death of said subject is reduced by from about 10% to about 20% compared to placebo. In some embodiments the risk of death of said subject is reduced about 15% compared to placebo.

In some embodiments the administration of liraglutide is a chronic treatment in which liraglutide is administered a) for at least 15 months, and wherein said method reduces or delays cardiovascular death (CV death); b) for at least 6 months (and optionally up to 54 months), and wherein said method reduces or delays non-fatal myocardial infarction (MI); c) for at least 40 months, and wherein said method reduces or delays non-fatal stroke; d) for at least 32 months (and optionally up to 56 months), and wherein said method reduces the need or risk of requiring coronary revascularisation; and/or for at least 17 months (and optionally up to 54 months), and wherein said method reduces or delays hospitalisation for heart failure.

In some embodiments the administration of liraglutide is a chronic treatment in which liraglutide is administered for at least 15 months, and wherein said method reduces or delays cardiovascular death (CV death). In some embodiments the administration of liraglutide is a chronic treatment in which liraglutide is administered for at least 12, or at least 18, months, and wherein said method reduces or delays cardiovascular death (CV death). In some embodiments the administration of liraglutide is a chronic treatment in which liraglutide is administered for at least 6 months (and optionally up to 54 months), and wherein said method reduces or delays non-fatal myocardial infarction (MI). In some embodiments the administration of liraglutide is a chronic treatment in which liraglutide is administered for at least 5, or 7 months, and wherein said method reduces or delays cardiovascular death (CV death). In some embodiments the administration of liraglutide is a chronic treatment in which liraglutide is administered for at least 40 months, and wherein said method reduces or delays non-fatal stroke. In some embodiments the administration of liraglutide is a chronic treatment in which liraglutide is administered for at least 36, or 40 months, and wherein said method reduces or delays cardiovascular death (CV death). In some embodiments the administration of liraglutide is a chronic treatment in which liraglutide is administered for at least 32 months (and optionally up to 56 months), and wherein said method reduces the need or risk of requiring coronary revascularisation. In some embodiments the administration of liraglutide is a chronic treatment in which liraglutide is administered for at least 30, or 35 months, and wherein said method reduces or delays cardiovascular death (CV death). In some embodiments the administration of liraglutide is a chronic treatment in which liraglutide is administered for at least 17 months (and optionally up to 54 months), and wherein said method reduces or delays hospitalisation for heart failure.

In some embodiments the administration of liraglutide is a chronic treatment in which liraglutide is administered for at least 15, or 20 months, and wherein said method reduces or delays cardiovascular death (CV death). In some embodiments the subject is less than 60 years of age. In some embodiments the subject has residence in Europe or Asia. In some embodiments the subject is of Asian ethnic origin. In some embodiments the subject has a BMI of more than 30 kg/m$^2$. In some embodiments the subject has a BMI of at least 30.4 kg/m$^2$. In some embodiments the subject has a HbA1c of more than 8.3%. In some embodiments the subject has a HbA1c at least 8.4%. In some embodiments the subject has a HbA1c of at least 9.0%. In some embodiments the subject was diagnosed with type 2 diabetes within a period of no more than 11 years prior to initiation of administration of liraglutide. In some embodiments the subject is at least 50 years of age and has a CV disease. In some embodiments the subject is at least 60 years of age and has a CV disease. In some embodiments the subject does not have chronic heart failure. In some embodiments the subject receives concomitant medication consisting of one oral antidiabetic drug (OAD). In some embodiments the subject has not previously received antidiabetic therapy. In some embodiments the subject does not receive additional antidiabetic therapy. In some embodiments the subject has moderate and/or severe renal impairment. In some embodiments the subject has moderate renal impairment. In some embodiments the subject has an eGFR of less than 60 mL/min/1.73 m$^2$, such as less than 40 mL/min/1.73 m$^2$ or less than 30 mL/min/1.73 m$^2$, wherein said eGFR may be determined by MDRD. In some embodiments the subject has an eGFR in the range of 30-59 mL/min/1.73 m$^2$, wherein said eGFR may be determined by MDRD. In some embodiments the subject has an eGFR in the range of more than 40 to less than 50 mL/min/1.73 m$^2$, wherein said eGFR may be determined by MDRD.

In some embodiments the terms "cardiovascular death" or "CV death" are used interchangeably herein to describe death, wherein the cause of death is selected from the group consisting of cardiovascular disease or is unknown. In some embodiments CV death is selected from the group consisting of death from cardiovascular causes, and deaths for which there was no clearly documented non-vascular cause. Death from cardiovascular causes may include sudden cardiac death, death due to acute myocardial infarction, death due to heart failure, and death due to stroke.

In some embodiments the terms "cardiovascular death" or "CV death" are used interchangeably herein to describe death, wherein the cause of death is selected from the group consisting of cardiovascular disease, also referred to herein as "CV death excluding death from unknown cause".

In some embodiments non-fatal MI is myocardial necrosis consistent with myocardial ischemia without death of the subject. In some embodiments MI is diagnosed based on the redefinitions suggested by the ESC (European Society of Cardiology)/ACCF (American College of Cardiology Foundation)/AHA (American Heart Association)/WHF (World Heart Federation) task force, as described in Thygesen K, et al. "Universal Definition of Myocardial Infarction." J Am Coll Cardiol 2007 Nov. 27; 50 (22): 2173-95.

In some embodiments coronary revascularisation is restoration of blood circulation in the heart, such as achieved by unblocking obstructed or disrupted blood vessels, or by surgically implanting replacements.

In some embodiments hospitalisation for unstable angina pectoris (UAP) is unplanned hospitalisation caused by ischemic symptoms suggestive of acute coronary syndrome and no elevation in cardiac biomarkers, including no elevation of troponin and cardiac biomarkers are negative for myocardial necrosis. Elevation of troponin may be at least 1 value above the 99th percentile of the upper reference limit, e.g. determined as Cardiac troponin I or Cardiac troponin T. Elevation of troponin may be Cardiac troponin I (cTnI) (e.g. determined by TnI-Ultra assay on the ADVIA Centaur XP immunoanalyzer, both Siemens Healthcare Diagnostics) of more than 0.04 ng/mL. In some embodiments UAP is not present when STEMI or NSTEMI are present (Criteria for STEMI: New ST segment elevation is present in 2 or more contiguous leads on the 12-lead ECG; Criteria for NSTEMI: ST segment elevation is absent in 2 or more contiguous leads on the 12-lead ECG; wherein said ECG shows manifestations of acute myocardial ischemia and may involve 1) ST elevation New ST elevation at the J-point in two contiguous leads with the cutoff points: ≥0.2 mV in men or ≥0.15 mV in women in leads V2-V3 and/or ≥0.1 mV in other leads; and/or 2) ST depression and T-wave changes New horizontal or down-sloping ST depression 0.05 mV in two contiguous leads; and/or T inversion ≥0.1 mV in two contiguous leads with prominent R-wave or R/S ratio >1). Acute coronary syndrome may involve at least one criteria selected from the group consisting of: New or worsening ST or T wave changes on ECG, wherein said ECG changes satisfy at least one of the following criteria for acute myocardial ischemia (in the absence of left ventricular hypertrophy and left bundle branch block): ST elevation; New transient (known to be <20 minutes) ST elevation at the J-point in two contiguous leads with the cut-off points: ≥0.2 mV in men or ≥0.15 mV in women in leads V2-V3 and/or ≥0.1 mV in other leads, ST depression and T-wave changes, New horizontal or down-sloping ST depression ≥0.05 mV in two contiguous leads; and/or T inversion ≥0.1 mV in two contiguous leads with prominent Rwave or R/S ratio >1; Evidence of ischemia on stress testing with cardiac imaging; Evidence of ischemia on stress testing without cardiac imaging but with angiographic evidence of ≥70% lesion and/or thrombus in an epicardial coronary artery or initiation/increased dosing of antianginal therapy; and Angiographic evidence of ≥70% lesion and/or thrombus in an epicardial coronary artery In some embodiments non-fatal stroke is stroke without death of the subject, wherein stroke includes transient ischemic attack, ischemic stroke, and hemorrhagic stroke. In some embodiments transient ischemic attack (TIA) is defined as a transient episode of neurological dysfunction caused by focal brain, spinal cord, or retinal ischemia, without acute infarction. In some embodiments ischemic stroke is defined as an acute episode of focal cerebral, spinal, or retinal dysfunction caused by an infarction of central nervous system tissue that results from a thrombus or embolus impairing central nervous system perfusion (not due to hemorrhage) and is documented by imaging; in addition, evidence of ischemic stroke obtained from autopsy can also confirm the diagnosis, and/or findings on lumbar puncture can be supportive to the diagnosis. In some embodiments hemorrhagic stroke is defined as an acute episode of focal or global cerebral, spinal, or retinal dysfunction caused by a nontraumatic intraparenchymal, intraventricular, or subarachnoid hemorrhage with documentation of cerebral hemorrhage on imaging (e.g., CT or MRI scan), i.e. intraparenchymal, intraparenchymal with penetration into the ventricles, intraventricular, or subarachnoidal hemorrhage; subdural and epidural bleedings are not included; in addition, evidence of hemorrhagic stroke obtained from autopsy can also confirm the diagnosis, and/or findings on lumbar puncture can be supportive to the diagnosis.

In some embodiments hospitalisation for heart failure is hospitalization defined as an admission to an inpatient unit or a visit to an emergency department that results in at least a 12 hour stay, wherein at least one of the following clinical manifestations of heart failure is present: New or worsening dyspnea, new or worsening orthopnea, new or worsening paroxysmal nocturnal dyspnea, new or worsening edema, new or worsening pulmonary basilar crackles, new or worsening jugular venous distension, new or worsening third heart sound or gallop rhythm, or radiological evidence of worsening heart failure. Hospitalisation for heart failure may also involve (i) additional and/or increased therapy, including a) initiation of intravenous diuretic, inotrope, or vasodilator therapy; b) uptitration of intravenous therapy, if already on therapy; c) initiation of mechanical or surgical intervention (mechanical circulatory support; d) heart transplantation or ventricular pacing to improve cardiac function), or the use of ultrafiltration, hemofiltration, or dialysis that is specifically directed at treatment of heart failure;

and/or (ii) biomarker results (e.g., brain natriuretic peptide) consistent with congestive heart failure will be supportive of this diagnosis.

In some embodiments the methods of the present invention reduce the occurrence of an event. In some embodiments "reduces or delays" when used herein with reference to the method of the invention is "reduces the risk of".

Subject and Subpopulations

The subject to be administered liraglutide according to the present invention may be human, such as an adult human. The subject to receive liraglutide administration according to the methods of the present invention may have type 2 diabetes and has (i) one or more vascular diseases selected from the group consisting of cardiovascular disease, cerebrovascular disease, peripheral vascular disease, chronic renal failure, and/or chronic heart failure, and/or (ii) one or more risk factors of vascular disease. In some embodiments the subject has type 2 diabetes and cardiovascular disease, cerebrovascular disease, peripheral vascular disease, chronic renal failure, and/or chronic heart failure. The subject may have type 2 diabetes and cardiovascular disease. The subject may have type 2 diabetes and cerebrovascular disease. The subject may have type 2 diabetes and peripheral vascular disease. The subject may have type 2 diabetes and chronic renal failure. The subject may have type 2 diabetes and chronic heart failure. In some embodiments the subject has type 2 diabetes and one or more risk factors of vascular disease. These vascular diseases may be referred to as concomitant, i.e. one or more vascular diseases are present in the subject at the same time as type 2 diabetes.

In some embodiments the subject is at least 50 years of age, such as at least 60 years of age.

In some embodiments the subject has $HbA_{1c}$ of at least 7.0%, e.g. prior to receiving liraglutide administration. In some embodiments the subject has $HbA_{1c}$ of more than 8.3%, e.g. prior to receiving liraglutide administration. In some embodiments the subject has $HbA_{1c}$ of at least 8.4%, e.g. prior to receiving liraglutide administration. In some embodiments the subject has $HbA_{1c}$ of at least 9.0%, e.g. prior to receiving liraglutide administration. $HbA_{1c}$ may be determined according to methods known in the art, for example as a percentage determined according to the method defined by the Diabetes Control and Complications Trial (DCCT), see New Engl J Med 1993; 329:977-986.

In some embodiments the subject is, except for liraglutide, anti-diabetic drug naive or treated with one or more oral anti-diabetic drugs (OADs) or treated with human NPH insulin or long-acting insulin analogue or premixed insulin, alone or in combination with OAD(s). The subject may be anti-diabetic drug naive. The subject may be treated with one or more oral anti-diabetic drugs (OADs). The subject may be treated with human NPH insulin or long-acting insulin analogue or premixed insulin, alone or in combination with OAD(s). In some embodiments the OAD may be selected from the group consisting of sulfonylureas, insulin secretagogues, thiazolidinediones, alpha-glucosidase inhibitors, dipeptidyl peptidase-4 inhibitors, sodium-glucose co-transporter-2 inhibitors, and combinations thereof. In some embodiments the OAD is sulfonylurea (e.g. glimepiride, glipizide, glyburide). In some embodiments the OAD is insulin secretagogues (e.g. biguanides such as metformin or meglitinides such as nateglinide). In some embodiments the OAD is thiazolidinediones (e.g. pioglitazone, rosiglitazone). In some embodiments the OAD is alpha-glucosidase inhibitors (e.g. acarbose, miglitol, voglibose). In some embodiments the OAD is sodium-glucose co-transporter-2 inhibitors (e.g. dapagliflozin, canagliflozin, empagliflozin). In some embodiments the OAD is dipeptidyl peptidase-4 inhibitors (e.g. sitagliptin). In some embodiments the OAD is not a dipeptidyl peptidase-4 inhibitor.

In some embodiments the subject (i) is at least 50 years of age and has cardiovascular disease, cerebrovascular disease, peripheral vascular disease, chronic renal failure, and/or chronic heart failure, or (ii) is at least 60 years of age and has one or more risk factors of vascular disease. In some embodiments the subject is at least 60 years of age and has cardiovascular disease, cerebrovascular disease, peripheral vascular disease, chronic renal failure, and/or chronic heart failure. In some embodiments the subject is at least 60 years of age and has cardiovascular disease, cerebrovascular disease, peripheral vascular disease, chronic renal failure, and/or chronic heart failure.

In some embodiments the subject a) (i) is at least 50 years of age and has one or more vascular diseases selected from the group consisting of cardiovascular disease, cerebrovascular disease, peripheral vascular disease, chronic renal failure, and/or chronic heart failure, or (ii) is at least 60 years of age and has risk factors of vascular disease; b) has $HbA_{1c}$ of at least 7.0%, e.g. at the time prior to receiving liraglutide administration; and c) is anti-diabetic drug naive or treated with one or more oral anti-diabetic drugs (OADs) or treated with human NPH insulin or long-acting insulin analogue or premixed insulin, alone or in combination with OAD(s).

In some embodiments the subject has renal impairment. In some embodiments the subject has moderate renal impairment (i.e. eGFR 30-59 per MDRD). In some embodiments the subject has severe renal impairment (i.e. eGFR <30 per MDRD). In some embodiments the subject has renal impairment, wherein the estimated glomerular filtration rate (eGFR) is <60, for example <60 mL/min/1.73 m² per Modification of Diet in Renal Disease (MDRD). In some embodiments the subject has eGFR of <60 mL/min/1.73 m² per MDRD. In some embodiments the subject has eGFR of <50 mL/min/1.73 m² per MDRD. In some embodiments the subject has eGFR of <40 mL/min/1.73 m² per MDRD. In some embodiments the subject has eGFR of <30 mL/min/1.73 m² per MDRD. In some embodiments the subject has eGFR of ≥10 mL/min/1.73 m² per MDRD. In some embodiments the estimated glomerular filtration rate (eGFR) is calculated based on serum creatinine concentration followed by either the equation Modification of Diet in Renal Disease (MDRD) or the Chronic Kidney Disease Epidemiology Collaboration (CKD-EPI), both involving variables for age, gender, and race of the subject. eGFR determined by MDRD may be referred to as eGFR-MDRD. eGFR determined by CKD-EPI may be referred to as eGFR-CKD-EPI. The eGFR-MDRD equation may be as defined in formula V: eGFR (mL/min/1.73 m²)=$175 \times (S_{cr})^{-1.154} \times (Age)^{-0.203} \times$ (0.742 if female)×(1.212 if African American) [V]. The CKD-EPI equation may be as defined in formula VI: eGFR=$141 \times min^{\alpha} \times max^{-1.209} \times 0.993^{Age} \times (1.018$ if female)× (1.159 if black) [VI], wherein "min" indicates the minimum of $S_{cr}/\kappa$ or 1, "max" indicates the maximum of $S_{cr}/\kappa$ or 1, $S_{cr}$ is serum creatinine in mg/dL, κ is 0.7 for females and 0.9 for males, and α is −0.329 for females or −0.411 for males.

In some embodiments the cardiovascular disease, cerebrovascular disease, peripheral vascular disease, chronic renal failure, and/or chronic heart failure are selected from the group consisting of myocardial infarction, stroke, transient ischaemic attack (TIA), coronary revascularisation, carotid revascularisation, peripheral arterial revascularisation, >50% stenosis of coronary arteries, >50% stenosis of carotid arteries, >50% stenosis of lower extremity arteries, history of symptomatic coronary heart disease (e.g. documented by positive exercise stress test or any cardiac imaging), unstable angina pectoris (e.g. with ECG (electrocardiogram) changes), asymptomatic cardiac ischemia (e.g. documented by positive nuclear imaging test or exercise test or dobutamine stress echo), chronic heart failure NYHA class and moderate-severe chronic renal failure (e.g. having clinically reached a stage corresponding to a glomerular filtration rate <60 mL/min/1.73 m² per Modification of Diet in Renal Disease (MDRD) or <60 mL/min per Cockroft-Gault formula). In some embodiments the cardiovascular disease, cerebrovascular disease, peripheral vascular disease, chronic renal failure, and/or chronic heart failure is selected from the group consisting of myocardial infarction, stroke, transient ischaemic attack (TIA), coronary revascularisation, carotid revascularisation, peripheral arterial revascularisation, wherein the event occurred before initiating liraglutide administration. In some embodiments the cardiovascular disease, cerebrovascular disease, peripheral vascular disease, chronic renal failure, and/or chronic heart failure may be selected from the group consisting of: a) myocardial infarction; b) stroke or prior transient ischaemic attack (TIA); c) coronary revascularisation, carotid revascularisation, or peripheral arterial revascularisation; d) >50% stenosis on angiography or other imaging of coronary, carotid or lower extremity arteries; e) history of symptomatic coronary heart disease documented by positive exercise stress test or any cardiac imaging, or unstable angina pectoris with ECG (electrocardiogram) changes; f) asymptomatic cardiac ischemia documented by positive nuclear imaging test or exercise test or dobutamine stress echo; g) chronic heart failure NYHA class and h) chronic renal failure, having clinically reached a stage corresponding to a glomerular filtration rate <60 mL/min/1.73 m² per Modification of Diet in Renal Disease (MDRD) or <60 mL/min per Cockroft-Gault formula. In some embodiments, the subject experienced the a) myocardial infarction; b) stroke or transient ischaemic attack (TIA); or c) coronary, carotid or peripheral arterial revascularisation as a prior event before the time of liraglutide administration. In some embodiments the cardiovascular disease, cerebrovascular disease, peripheral vascular disease, chronic renal failure, and/or chronic heart failure is selected from the group consisting of prior myocardial infarction, prior stroke, and prior transient ischaemic attack (TIA). In some embodiments the cardiovascular disease, cerebrovascular disease, peripheral vascular disease, chronic renal failure, and/or chronic heart failure is selected from the group consisting of prior coronary revascularisation, prior carotid revascularisation, and prior peripheral arterial revascularisation. In some embodiments the cardiovascular disease, cerebrovascular disease, peripheral vascular disease, chronic renal failure, and/or chronic heart failure is selected from the group consisting of >50% stenosis of coronary arteries, >50% stenosis of carotid arteries, and >50% stenosis of lower extremity arteries. In some embodiments the cardiovascular disease, cerebrovascular disease, peripheral vascular disease, chronic renal failure, and/or chronic heart failure is selected from the group consisting of history of symptomatic coronary heart disease (e.g. documented by positive exercise stress test or any cardiac imaging), and unstable angina pectoris (e.g. with ECG (electrocardiogram) changes). In some embodiments the cardiovascular disease, cerebrovascular disease, peripheral vascular disease, chronic renal failure, and/or chronic heart failure is selected from the group consisting of asymptomatic cardiac ischemia (e.g. documented by positive nuclear imaging test or exercise test or dobutamine stress echo). In some embodiments the cardiovascular disease, cerebrovascular disease, peripheral vascular disease, chronic renal failure, and/or chronic heart failure is selected from the group consisting of chronic heart failure NYHA class II-III. In some embodiments the cardiovascular disease, cerebrovascular disease, peripheral vascular disease, chronic renal failure, and/or chronic heart failure is selected from the group consisting of moderate-severe chronic renal failure (e.g. having clinically reached a stage corresponding to a glomerular filtration rate <60 mL/min/1.73 m² per Modification of Diet in Renal Disease (MDRD) or <60 mL/min per Cockroft-Gault formula). In some embodiments the "prior" as used herein refers to before liraglutide administration.

The glomerular filtration rate may alternatively be determined by the "Cockroft-Gault formula" may be as defined by Formula III: CrCl (mL/min)=(N×[140−age (years)]× weight*(kg))/Serum creatinine (µM) [III], wherein CrCl is the Cockcroft and Gault creatinine clearance, wherein N is 1.23 for males and 1.04 for females, and wherein if actual weight is greater than 120% IBW then weight is the ideal body weight (IBW) as defined in Formula IIIa: IBW (kg)= (no of inches over 5 ft×2.3)+M [IIIa], wherein M is 50 for males and 45.5 for females.

Heart failure exists in different degrees of severity. The most commonly used classification system of heart failure is the New York Heart Association Functional Classification (also referred to as "NYHA"). NYHA categorises subjects in one of four classes I-IV (Table A), based on their degree of limitation during physical activity, and optionally an additional subgroup A-D based on objective assessments, for further details see The Criteria Committee of the New York Heart Association. Nomenclature and Criteria for Diagnosis of Diseases of the Heart and Great Vessels. 9th ed. Boston, Mass.: Little, Brown & Co; 1994:253-256). In some embodiments the subject has heart failure NYHA class I-III, such as class I, class II or class III.

TABLE A

NYHA class I-IV criteria

| NYHA Class | Functional Capacity of the subject |
| --- | --- |
| I | Subjects with cardiac disease but without resulting limitation of physical activity. Ordinary physical activity does not cause undue fatigue, palpitation, dyspnea, or anginal pain. |
| II | Subjects with cardiac disease resulting in slight limitation of physical activity. They are comfortable at rest. Ordinary physical activity results in fatigue, palpitation, dyspnea, or anginal pain. |
| III | Subjects with cardiac disease resulting in marked limitation of physical activity. They are comfortable at rest. Less than ordinary activity causes fatigue, palpitation, dyspnea, or anginal pain. |
| IV | Subjects with cardiac disease resulting in inability to carry on any physical activity without discomfort. Symptoms of heart failure or the anginal syndrome may be present even at rest. If any physical activity is undertaken, discomfort is increased. |

The "cardiovascular disease, cerebrovascular disease, peripheral vascular disease, chronic renal failure, and/or chronic heart failure" may be myocardial infarction. The "cardiovascular disease, cerebrovascular disease, peripheral vascular disease, chronic renal failure, and/or chronic heart failure" may be stroke or prior transient ischaemic attack (TIA). The "cardiovascular disease, cerebrovascular disease, peripheral vascular disease, chronic renal failure, and/or chronic heart failure" may be coronary, carotid or peripheral arterial revascularisation. The "cardiovascular disease, cerebrovascular disease, peripheral vascular disease, chronic renal failure, and/or chronic heart failure" may be >50% stenosis on angiography or other imaging of coronary, carotid or lower extremity arteries. The "cardiovascular disease, cerebrovascular disease, peripheral vascular disease, chronic renal failure, and/or chronic heart failure" may be history of symptomatic coronary heart disease documented by positive exercise stress test or any cardiac imaging, or unstable angina pectoris with ECG changes. The "cardiovascular disease, cerebrovascular disease, peripheral vascular disease, chronic renal failure, and/or chronic heart failure" may be asymptomatic cardiac ischemia documented by positive nuclear imaging test or exercise test or dobutamine stress echo. The "cardiovascular disease, cerebrovascular disease, peripheral vascular disease, chronic renal failure, and/or chronic heart failure" may be chronic heart failure NYHA class II-III. The "cardiovascular disease, cerebrovascular disease, peripheral vascular disease, chronic renal failure, and/or chronic heart failure" may be chronic renal failure, having clinically reached a stage corresponding to a glomerular filtration rate <60 mL/min/1.73 m² per Modification of Diet in Renal Disease (MDRD) or <60 mL/min per Cockroft-Gault formula.

In some embodiments the subject has a BMI of at least 30 kg/m². BMI (body mass index) is a measure of body fat based on height and weight. The formula for calculation is BMI=(weight in kilograms)/(height in meters)². In some embodiments the subject has a BMI in the range of 30-50 kg/m². In some embodiments the subject has a BMI of at least 33 kg/m². In some embodiments the subject has a BMI of at least 35 kg/m². In some embodiments the subject has a BMI of at least 37 kg/m². In some embodiments the subject has a BMI of at least 40 kg/m². In some embodiments the subject has a BMI of up to 45 kg/m². In some embodiments the subject has a BMI of up to 40 kg/m².

In some embodiments the term "residence" of a subject as used herein refers to the jurisdiction in which said subject has its address registered with the authorities of said jurisdiction, e.g. Europe or Asia.

In some embodiments the subject does not have type 1 diabetes. In some embodiments the subject does not receive administration of a GLP-1 receptor agonist (exenatide or other) or pramlintide or any dipeptidyl peptidase 4 (DPP-4) inhibitor prior to initiating administration of liraglutide according to the present invention. In some embodiments the subject does not receive administration of insulin other than insulin selected from the group consisting of human neutral protamine hagedorn (NPH) insulin, long-acting insulin analogue or premixed insulin. In some embodiments, and in connection with intercurrent illness, the subject receives short-term administration of insulin other than insulin selected from the group consisting of human NPH insulin, long-acting insulin analogue or premixed insulin. Acute decompensation of glycaemic control requiring immediate intensification of treatment to prevent acute complications of diabetes (e.g., diabetic ketoacidosis) in the previous 3 months. In some embodiments the subject does not have an acute coronary or cerebrovascular event in the previous 14 days. In some embodiments the subject does not receive continuous renal replacement therapy. In some embodiments the subject does not have end-stage liver disease. In some embodiments the subject does not have chronic heart failure NYHA IV. In some embodiments the subject does not have a prior solid organ transplant or awaiting solid organ transplant. In some embodiments the subject does not have family or personal history of multiple endocrine neoplasia type 2 (MEN2) or familial medullary thyroid carcinoma (FMTC). In some embodiments the subject does not have personal history of non-familial medullary thyroid carcinoma. In some embodiments the subject does not have malignant neoplasm requiring chemotherapy, surgery, radiation or palliative therapy in the previous 5 years. In some embodiments the subject has intraepithelial squamous cell carcinoma of the skin (Bowen's disease) treated with topical 5-fluorouracil (5FU) and subjects with basal cell skin cancer.

Liraglutide

Liraglutide is the GLP-1 receptor agonist Arg34,Lys26-(N-epsilon-(gamma-L-glutamyl(N-alfa-hexadecanoyl)))-GLP-1(7-37). Liraglutide may be prepared as described in Example 37 of WO98/08871.

Pharmaceutical Composition

Liraglutide may be administered in the form of a pharmaceutical composition. The pharmaceutical composition may comprise liraglutide in a concentration from 0.1 mg/ml to 100 mg/ml. In some embodiments the pharmaceutical composition comprises 0.01-50 mg, or 0.01-20 mg, or 0.01-10 mg/ml liraglutide. In some embodiments the pharmaceutical composition comprises 1-20 mg/ml liraglutide.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more pharmaceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. liraglutide. The excipient may be an inert substance, an inactive substance, and/or a not medicinally active substance.

In some embodiments the pharmaceutical composition comprises a phosphate buffer, such as a sodium phosphate buffer, e.g. disodium phosphate. In some embodiments the pharmaceutical composition comprises an isotonic agent, such as propylene glycol. In some embodiments the pharmaceutical composition comprises a preservative, such as phenol.

The pharmaceutical composition may be in the form of a solution or a suspension. In some embodiments the pharmaceutical composition is aqueous composition, such as an aqueous solution or an aqueous suspension. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. An aqueous composition may comprise at least 50% w/w water, or at least 60%, 70%, 80%, or even at least 90% w/w of water. In some embodiments the pharmaceutical composition has a pH in the range of 7.5-9.0.

In some embodiments liraglutide is administered in the form of a pharmaceutical composition comprising about 1-20 mg/ml liraglutide, about 2-15 mM phosphate buffer, about 2-25 mg/ml propylene glycol, about 1-18 mg/ml phenol, and has a pH in the range of 7.5-9.0. In some embodiments liraglutide is administered in the form of a pharmaceutical composition comprising about 6 mg/ml liraglutide, about 1.42 mg/ml disodium phosphate dihydrate, about 14.0 mg/ml propylene glycol, about 5.5 mg/ml phenol, and has pH of about 8.15. In some embodiments liraglutide is administered in the form of a pharmaceutical composition comprising 6 mg/ml liraglutide, 1.42 mg/ml disodium phosphate dihydrate, 14.0 mg/ml propylene glycol, 5.5 mg/ml phenol, and has pH of 8.15.

Administration Regimen

Liraglutide may be administered in a therapeutically effective amount, such as an amount therapeutically effective to treat type 2 diabetes. The therapeutically effective amount of liraglutide can be assessed by a medical doctor. The dosage of liraglutide may be in the range from 0.1 to 10 mg.

Liraglutide may be administered once daily. In some embodiments liraglutide is administered once daily at any time in the day. In some embodiments the daily dosage of liraglutide is in the range from 0.4 to 4.0 mg, such as in the range from 0.4 to 2.0 mg. In some embodiments the daily dosage of liraglutide is selected from the group consisting of 0.6, 1.2, and 1.8 mg. In some embodiments the daily dosage of liraglutide is 3.0 mg.

In some embodiments the term "chronic treatment" as used herein with reference to liraglutide means administration in an amount and frequency to provide a therapeutic effect. In some embodiments the term "chronic treatment" as used herein with reference to liraglutide means once daily administration 0.4-4.0 mg, such as 0.6, 1.2, or 1.8 mg, liraglutide.

Liraglutide may be administered via parenteral administration, for example subcutaneous injection. Liraglutide may be administered using a pen-injector, such as a 3 ml disposable pen-injector.

Unless otherwise states, ranges herein include their end points. In some embodiments the term "a" means "one or more". In some embodiments, and unless otherwise indicated in the specification, terms presented in singular form also include the plural situation. Herein the term "about" means±10% of the value referred to, and includes the value.

Non-Limiting Embodiments of the Invention

Non-limiting embodiments of the invention include:

1. A method of treating type 2 diabetes, comprising administering liraglutide in a therapeutically effective amount to a subject in need thereof, wherein said subject has (i) one or more vascular diseases selected from the group consisting of cardiovascular disease, cerebrovascular disease, peripheral vascular disease, chronic renal failure, and chronic heart failure, and/or (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9; wherein said method reduces or delays development of a major adverse cardiovascular event (MACE).

2. A method of treating type 2 diabetes, comprising administering liraglutide in a therapeutically effective amount to a subject in need thereof, wherein said subject has (i) one or more vascular diseases selected from the group consisting of cardiovascular disease, cerebrovascular disease, peripheral vascular disease, chronic renal failure, and chronic heart failure, and/or (ii) one or more risk factors of vascular disease selected from the group consisting of microalbuminuria, proteinuria, hypertension, left ventricular hypertrophy, left ventricular systolic dysfunction, and ankle/brachial index <0.9; wherein said method reduces the risk of said subject developing a major adverse cardiovascular event (MACE).

3. A method of treating type 2 diabetes, comprising administering liraglutide in a therapeutically effective amount to a subject in need thereof, wherein said subject has (i) one or more vascular diseases selected from the group consisting of cardiovascular disease, cerebrovascular disease, peripheral vascular disease, chronic renal failure, and chronic heart failure, and/or (ii) one or more risk factors of vascular disease selected from the group consisting of a) microalbuminuria or proteinuria; b) hypertension and/or left ventricular hypertrophy by ECG or imaging; c) left ventricular systolic or diastolic dysfunction by imaging; and d) ankle/brachial index <0.9; wherein said method reduces the risk of said subject developing a major adverse cardiovascular event (MACE).

4. The method according to any one of the preceding claims, wherein said subject has (i) vascular disease selected from the group consisting of cardiovascular disease, cerebrovascular disease, peripheral vascular disease, chronic renal failure, and chronic heart failure.

5. The method according to any one of the preceding claims, wherein said subject has (ii) one or more risk factors of vascular disease selected from the group consisting of microalbuminuria, proteinuria, hypertension, left ventricular hypertrophy, left ventricular systolic dysfunction, left ventricular diastolic dysfunction, and ankle/brachial index <0.9.

6. The method according to any one of the preceding claims, wherein said subject has (ii) one or more risk factors of vascular disease selected from the group consisting of a) microalbuminuria or proteinuria; b) hypertension and/or left ventricular hypertrophy by ECG or imaging; c) left ventricular systolic or diastolic dysfunction by imaging; and d) ankle/brachial index <0.9.

7. The method according to any one of the preceding claims, wherein said vascular disease and/or said one or more risk factors of vascular disease was present before initiation of liraglutide administration.

8. The method according to any one of the preceding claims, wherein said MACE is selected from the group consisting of CV death, non-fatal MI, non-fatal stroke, coronary revascularisation, hospitalisation for heart failure, and hospitalisation for unstable angina pectoris.

9. The method according to any one of the preceding claims, wherein said MACE is reduced or delayed by at least 1% compared to placebo.

10. The method according to any one of the preceding claims, wherein said MACE is reduced or delayed by from about 1% to about 3% compared to placebo.

11. The method according to any one of the preceding claims, wherein said MACE is reduced about 2.4% compared to placebo.

12. The method according to any one of the preceding claims, wherein the first MACE is reduced or delayed by at least 1% compared to placebo.

13. The method according to any one of the preceding claims, wherein first MACE is reduced or delayed by from about 1% to about 3% compared to placebo.

14. The method according to any one of the preceding claims, wherein first MACE is reduced about 2.4% compared to placebo.

15. The method according to any one of the preceding claims, wherein said MACE is selected from the group consisting of CV death, non-fatal MI, non-fatal stroke, coronary revascularisation, and hospitalisation for heart failure.

16. The method according to any one of the preceding claims, wherein said MACE is selected from the group consisting of CV death, non-fatal MI, and non-fatal stroke.
17. The method according to any one of the preceding claims, wherein said MACE is reduced or delayed by at least 10% compared to placebo.
18. The method according to any one of the preceding claims, wherein said MACE is reduced or delayed by from about 10% to about 15% compared to placebo.
19. The method according to any one of the preceding claims, wherein said MACE is reduced or delayed about 13% compared to placebo.
20. The method according to any one of the preceding claims, wherein said MACE has a hazard ratio of about 0.87 compared to placebo.
21. The method according to any one of the preceding claims, wherein said MACE has a hazard ratio of 0.87 with a 95% CI of (0.78; 0.97) compared to placebo.
22. The method according to any one of the preceding claims, wherein the risk of said subject developing a MACE is reduced by at least 10% compared to placebo.
23. The method according to any one of the preceding claims, wherein the risk of said subject developing a MACE is reduced by from about 10% to about 15% compared to placebo.
24. The method according to any one of the preceding claims, wherein the risk of said subject developing a MACE is reduced about 13% compared to placebo.
25. The method according to any one of the preceding claims, wherein the subject developing a MACE has a hazard ratio of about 0.87 compared to placebo.
26. The method according to any one of the preceding claims, wherein the subject developing a MACE has a hazard ratio of 0.87 with a 95% CI of (0.78; 0.97) compared to placebo.
27. The method according to any one of the preceding claims, wherein said subject developing its first MACE is reduced or delayed by at least 10% compared to placebo.
28. The method according to any one of the preceding claims, wherein said MACE is reduced or delayed by from about 10% to about 15% compared to placebo.
29. The method according to any one of the preceding claims, wherein said first MACE is reduced or delayed about 13% compared to placebo.
30. The method according to any one of the preceding claims, wherein the subject developing its first MACE has a hazard ratio of about 0.87 compared to placebo.
31. The method according to any one of the preceding claims, wherein the subject developing its first MACE has a hazard ratio of 0.87 with a 95% CI of (0.78; 0.97) compared to placebo.
32. The method according to any one of the preceding claims, wherein said MACE is CV death.
33. The method according to any one of the preceding claims, wherein said CV death is reduced by at least 10% compared to placebo.
34. The method according to any one of the preceding claims, wherein said CV death is reduced or delayed by from about 10% to about 35% compared to placebo.
35. The method according to any one of the preceding claims, wherein said CV death is reduced by from about 15% to about 30% compared to placebo.
36. The method according to any one of the preceding claims, wherein said CV death is reduced or delayed by about 22% compared to placebo.
37. The method according to any one of the preceding claims, wherein said MACE is non-fatal MI.
38. The method according to any one of the preceding claims, wherein said non-fatal MI is reduced or delayed by at least 8% compared to placebo.
39. The method according to any one of the preceding claims, wherein said non-fatal MI is reduced or delayed by from about 8% to about 20% compared to placebo.
40. The method according to any one of the preceding claims, wherein said non-fatal MI is reduced or delayed by from about 10% to about 15% compared to placebo.
41. The method according to any one of the preceding claims, wherein said non-fatal MI is reduced or delayed by about 12% compared to placebo.
42. The method according to any one of the preceding claims, wherein said MACE is non-fatal stroke.
43. The method according to any one of the preceding claims, wherein said non-fatal stroke is reduced or delayed by at least 7% compared to placebo.
44. The method according to any one of the preceding claims, wherein said non-fatal stroke is reduced or delayed by from about 8% to about 20% compared to placebo.
45. The method according to any one of the preceding claims, wherein said non-fatal stroke is reduced or delayed by from about 9% to about 15% compared to placebo.
46. The method according to any one of the preceding claims, wherein said non-fatal stroke is reduced or delayed by about 11% compared to placebo.
47. The method according to any one of the preceding claims, wherein said MACE is coronary revascularisation.
48. The method according to any one of the preceding claims, wherein said coronary revascularisation is reduced or delayed by at least 5% compared to placebo.
49. The method according to any one of the preceding claims, wherein said coronary revascularisation is reduced or delayed by from about 5% to about 20% compared to placebo.
50. The method according to any one of the preceding claims, wherein said coronary revascularisation is reduced or delayed by from about 7% to about 15% compared to placebo.
51. The method according to any one of the preceding claims, wherein said coronary revascularisation is reduced or delayed by about 9% compared to placebo.
52. The method according to any one of the preceding claims, wherein said MACE is hospitalisation for heart failure.
53. The method according to any one of the preceding claims, wherein said hospitalisation for heart failure is reduced or delayed by at least 5% compared to placebo.
54. The method according to any one of the preceding claims, wherein said hospitalisation for heart failure is reduced or delayed by from about 8% to about 20% compared to placebo.
55. The method according to any one of the preceding claims, wherein said hospitalisation for heart failure is reduced or delayed by about 13% compared to placebo.
56. The method according to any one of the preceding claims, wherein said hospitalisation for heart failure is reduced or delayed by at least 10% compared to placebo.

57. The method according to any one of the preceding claims, wherein said hospitalisation for heart failure is reduced or delayed by from about 10% to about 35% compared to placebo.
58. The method according to any one of the preceding claims, wherein said hospitalisation for heart failure is reduced or delayed by from about 15% to about 30% compared to placebo.
59. The method according to any one of the preceding claims, wherein said hospitalisation for heart failure is reduced or delayed by about 23% compared to placebo.
60. The method according to any one of the preceding claims, wherein said MACE is hospitalisation for unstable angina pectoris.
61. The method according to any one of the preceding claims, wherein said hospitalisation for unstable angina pectoris is reduced or delayed by at least 1% compared to placebo.
62. The method according to any one of the preceding claims, wherein said hospitalisation for unstable angina pectoris is reduced or delayed by from about 1% to about 5% compared to placebo.
63. The method according to any one of the preceding claims, wherein said hospitalisation for unstable angina pectoris is reduced or delayed by about 2% compared to placebo.
64. The method according to any one of the preceding claims, wherein said MACE is
    a. CV death, and wherein said CV death is reduced or delayed by from about 10% to about 35% compared to placebo;
    b. non-fatal MI, and wherein said non-fatal MI is reduced or delayed by from about 8% to about 20% compared to placebo;
    c. non-fatal stroke, and wherein said non-fatal stroke is reduced or delayed by from about 8% to about 20% compared to placebo; and/or
    d. hospitalisation for heart failure, and wherein said hospitalisation for heart failure is reduced or delayed by from about 10% to about 35% compared to placebo.
65. The method according to any one of the preceding claims, wherein said MACE is
    a. CV death, and wherein said CV death is reduced or delayed by about 22% compared to placebo;
    b. non-fatal MI, and wherein said non-fatal MI is reduced or delayed by about 12% compared to placebo;
    c. non-fatal stroke, and wherein said non-fatal stroke is reduced or delayed by about 11% compared to placebo; and/or
    d. hospitalisation for heart failure, and wherein said hospitalisation for heart failure is reduced or delayed by about 13% compared to placebo.
66. The method according to any one of the preceding claims, wherein said MACE is
    a. CV death, and wherein said CV death is reduced or delayed by about 22% compared to placebo;
    b. non-fatal MI, and wherein said non-fatal MI is reduced or delayed by about 12% compared to placebo;
    c. non-fatal stroke, and wherein said non-fatal stroke is reduced or delayed by about 11% compared to placebo; and/or
    d. hospitalisation for heart failure, and wherein said hospitalisation for heart failure is reduced or delayed by about 23% compared to placebo.
67. The method according to any one of the preceding claims, wherein said method further reduces the risk of death of said subject, wherein the cause of said death is any cause.
68. The method according to any one of the preceding claims, wherein the risk of death of said subject is reduced by at least 10% compared to placebo.
69. The method according to any one of the preceding claims, wherein the risk of death of said subject is reduced by from about 10% to about 20% compared to placebo.
70. The method according to any one of the preceding claims, wherein the risk of death of said subject is reduced about 15% compared to placebo.
71. The method according to any one of the preceding claims, wherein said administration of liraglutide is a chronic treatment in which liraglutide is administered:
    a. for at least 15 months, and wherein said method reduces or delays cardiovascular death (CV death);
    b. for at least 6 months (and optionally up to 54 months), and wherein said method reduces or delays non-fatal myocardial infarction (MI);
    c. for at least 40 months, and wherein said method reduces or delays non-fatal stroke;
    d. for at least 32 months (and optionally up to 56 months), and wherein said method reduces the risk of requiring coronary revascularisation; and/or
    e. for at least 17 months (and optionally up to 54 months), and wherein said method reduces or delays hospitalisation for heart failure.
72. The method according to any one of the preceding claims, wherein said administration of liraglutide is a chronic treatment in which liraglutide is administered for at least 15 months, and wherein said method reduces or delays cardiovascular death (CV death).
73. The method according to any one of the preceding claims, wherein said administration of liraglutide is a chronic treatment in which liraglutide is administered for at least 12, or at least 18, months, and wherein said method reduces or delays cardiovascular death (CV death).
74. The method according to any one of the preceding claims, wherein said administration of liraglutide is a chronic treatment in which liraglutide is administered for at least 6 months (and optionally up to 54 months), and wherein said method reduces or delays non-fatal myocardial infarction (MI).
75. The method according to any one of the preceding claims, wherein said administration of liraglutide is a chronic treatment in which liraglutide is administered for at least 5, or 7 months, and wherein said method reduces or delays cardiovascular death (CV death).
76. The method according to any one of the preceding claims, wherein said administration of liraglutide is a chronic treatment in which liraglutide is administered for at least 40 months, and wherein said method reduces or delays non-fatal stroke.
77. The method according to any one of the preceding claims, wherein said administration of liraglutide is a chronic treatment in which liraglutide is administered for at least 36, or 40 months, and wherein said method reduces or delays cardiovascular death (CV death).
78. The method according to any one of the preceding claims, wherein said administration of liraglutide is a chronic treatment in which liraglutide is administered for at least 32 months (and optionally up to 56 months), and wherein said method reduces the risk of requiring coronary revascularisation.
79. The method according to any one of the preceding claims, wherein said administration of liraglutide is a chronic treatment in which liraglutide is administered for at least 30, or 35 months, and wherein said method reduces or delays cardiovascular death (CV death).
80. The method according to any one of the preceding claims, wherein said administration of liraglutide is a chronic treatment in which liraglutide is administered for at least 17 months (and optionally up to 54 months), and wherein said method reduces or delays hospitalisation for heart failure.
81. The method according to any one of the preceding claims, wherein said administration of liraglutide is a chronic treatment in which liraglutide is administered for at least 15, or 20 months, and wherein said method reduces or delays cardiovascular death (CV death).
82. The method according to any one of the preceding claims, wherein said subject is less than 60 years of age.
83. The method according to any one of the preceding claims, wherein said subject has residence in Europe or Asia.
84. The method according to any one of the preceding claims, wherein said subject is of Asian ethnic origin.
85. The method according to any one of the preceding claims, wherein said subject has a BMI of more than 30 kg/m$^2$.
86. The method according to any one of the preceding claims, wherein said subject has a BMI of at least 30.4 kg/m$^2$.
87. The method according to any one of the preceding claims, wherein said subject has a HbA1c of more than 8.3%.
88. The method according to any one of the preceding claims, wherein said subject has a HbA1c of at least 8.4%.
89. The method according to any one of the preceding claims, wherein said subject has a HbA1c of at least 9.0%.
90. The method according to any one of the preceding claims, wherein said subject has had type 2 diabetes within a period of no more than 11 years prior to initiation of administration of liraglutide according to the methods described herein.
91. The method according to any one of the preceding claims, wherein said subject is at least 50 years of age and has a CV disease.
92. The method according to any one of the preceding claims, wherein said subject is at least 60 years of age and has a CV disease.
93. The method according to any one of the preceding claims, wherein said subject does not have chronic heart failure.
94. The method according to any one of the preceding claims, wherein said subject receives concomitant medication consisting of one oral antidiabetic drug (OAD).
95. The method according to any one of the preceding claims, wherein said subject has not previously received antidiabetic therapy.
96. The method according to any one of the preceding claims, wherein said subject does not receive additional antidiabetic therapy.
97. The method according to any one of the preceding claims, wherein said subject has moderate and/or severe renal impairment.
98. The method according to any one of the preceding claims, wherein said subject has moderate renal impairment.
99. The method according to any one of the preceding claims, wherein said subject has an eGFR of less than 60 mL/min/1.73 m$^2$, such as less than 40 mL/min/1.73 m$^2$ or less than 30 mL/min/1.73 m$^2$, wherein said eGFR may be determined by MDRD.
100. The method according to any one of the preceding claims, wherein said subject has an eGFR in the range of 30 to 59 mL/min/1.73 m$^2$, wherein said eGFR may be determined by MDRD.
101. The method according to any one of the preceding claims, wherein said subject has an eGFR in the range of more than 40 to less than 50 mL/min/1.73 m$^2$, wherein said eGFR may be determined by MDRD.
102. The method according to any one of the preceding claims, wherein liraglutide is administered once daily.
103. The method according to any one of the preceding claims, wherein liraglutide is administered once daily in an amount in the range of 0.4-2.0 mg per day, such as 0.6, 1.2, or 1.8 mg per day.
104. The method according to any one of the preceding claims, wherein liraglutide is administered in the form of a pharmaceutical composition comprising about 1-20 mg/ml liraglutide, about 2-15 mM phosphate buffer, about 2-25 mg/ml propylene glycol, about 1-18 mg/ml phenol, and has a pH in the range of 7.5-9.0.
105. The method according to any one of the preceding claims, wherein liraglutide is administered in the form of a pharmaceutical composition comprising about 6 mg/ml liraglutide, about 1.42 mg/ml disodium phosphate dihydrate, about 14.0 mg/ml propylene glycol, about 5.5 mg/ml phenol, and has pH of about 8.15.
106. The method according to any one of the preceding claims, wherein liraglutide is administered in the form of a pharmaceutical composition comprising 6 mg/ml liraglutide, 1.42 mg/ml disodium phosphate dihydrate, 14.0 mg/ml propylene glycol, 5.5 mg/ml phenol, and has pH of 8.15.

EXAMPLES

List of Abbreviations
  MACE: Major adverse cardiovascular event
  HbA$_{1c}$: Glycosylated haemoglobin
  GLP-1: Glucagon-like peptide-1
  BMI: Body mass index
  N: Number of subjects
  CV: Cardiovascular
  OAD: Oral antidiabetic drug
  TIA: Transient ischaemic attack
  CI: Confidence interval
  CKD-EPI: Chronic Kidney Disease Epidemiology Collaboration
  MDRD: modification of diet in renal disease
  MI: Myocardial infarction.
  UAP: Unstable angina pectoris.
Clinical Trial: Materials and Methods
  A long-term, multi-centre, international, randomised double-blind, placebo-controlled trial with 9340 human subjects was carried out with treatment for at least 3.5 years and up to 5 years per subject; and this trial concerned the incidence of cardiovascular events in adult human subjects with type 2 diabetes that were at high risk for cardiovascular events, including such subjects with existing cardiovascular disease. The primary objective of this trial was to determine the long term effect of treatment with liraglutide compared to placebo on cardiovascular events in subjects with type 2 diabetes. The secondary objective was to assess the efficacy and safety with regard to clinically important events or other surrogate parameters of treatment with liraglutide compared to placebo in adults with type 2 diabetes that were at high risk for cardiovascular events. All trial endpoints were collected and assessed throughout the entire duration of the trial. Subject inclusion and exclusion criteria were as described in Table 2. The subject's characteristics, cardiovascular risk profile, renal function, cardiovascular medication, and antidiabetic treatment regimens of the randomised subjects at baseline were as shown in Tables 3a-e. Overall trial duration was planned as 18 months of recruitment period followed by 42 months of treatment from last subject randomised. The trial started with an open-label run-in period of two weeks with placebo following which subjects were randomised in a 1:1 manner to receive liraglutide or placebo as an add-on to their standard of care (SOC) treatment. The subject's SOC treatment was as shown in Table 4. After randomisation, treatment with liraglutide or placebo was double-blind throughout the trial. Subjects were started on 0.6 mg of liraglutide or placebo. The term "placebo" as used herein refers to a formulation identical to the liraglutide formulation except not comprising liraglutide and the placebo was administered in the volume used in the equivalent liraglutide dosage. Dose escalation of liraglutide or placebo proceeded to 1.2 mg after one week followed by dose escalation to 1.8 mg after one week. After the dose escalation, 95% of subjects received 1.8 mg of liraglutide or placebo, 5% of subjects received 1.2 mg of liraglutide or placebo, and 5% of subjects received 0.6 mg of liraglutide or placebo. Dose increase period could be extended if required in view of a subject's tolerance to the trial product (i.e. liraglutide or placebo). The dosage could be reduced at any time in the trial if required by the subject's tolerance to the trial product. Subjects received liraglutide or placebo by subcutaneous administrations once daily in addition to the subject's standard treatment at a maximum dose of 1.8 mg liraglutide or placebo. The subcutaneous injection was made either in the abdomen, thigh or upper arm. The formulations were administered in the form of an aqueous solution comprising liraglutide or placebo, both using a 3 ml disposable pen-injector. This pen-injector was identical for the liraglutide and placebo administrations. This aqueous solution contained 6.0 mg/ml liraglutide, 1.42 mg/ml disodium phosphate dihydrate, 14.0 mg/ml propylene glycol, 5.5 mg/ml phenol, and had pH 8.15. Liraglutide may be prepared as described in WO98/08871.

The term "baseline" herein (e.g. used as part of "baseline characteristics" or "baseline cardiovascular risk profile") may refer to the level of a certain parameter (e.g. level of HbA1c) by the determination made in connection with the medical visit at the time of randomisation of the subject. In some embodiments the term baseline refers to a parameter before initiating administration of liraglutide, e.g. the history of a certain event in a subject.

The results of this trial may be presented herein as a number or fraction of subjects experiencing an event. Alternatively, the results of this trial may be presented with hazard ratios estimated in a Cox proportional hazard model, which is the standard statistical model used for estimating time to an event. The term "hazard ratio" (also referred to as "HR") as used herein means the instantaneous risk ratio of experiencing an event when administered liraglutide compared to placebo which are the two treatments in this trial. An upper limit of the 95% confidence interval (CI) for the HR of less than 1.00 means that the estimated treatment ratio between liraglutide and placebo with respect to the event of interests is statistically significant in favour of liraglutide on a 5% significance level. A 5% significance level is the standard level for investigating significance in clinical trials. For example, a HR value of 0.78 for time to first CV death with a 95% CI of (0.66; 0.94) means that liraglutide provides an estimated 22% risk reduction of experiencing CV death at any given point in time compared to placebo and this risk reduction is statistically significant because 0.94 is less than 1.00.

"Cardiovascular death" (also referred to as "CV death") was registered in case of death, wherein the cause of death was selected from the group consisting of cardiovascular disease or unknown.

TABLE 2

Subject inclusion and exclusion criteria (all inclusion criteria were fulfilled for eligible subjects; one or more exclusion criteria were fulfilled for subjects to be excluded; however, 150 patients violated at least one inclusion or exclusion criteria)

| Inclusion Criteria | Exclusion Criteria |
| --- | --- |
| Men or women with type 2 diabetes Age ≥50 years at screening and concomitant cardiovascular disease, cerebrovascular disease, peripheral vascular disease, chronic renal failure, and/or chronic heart failure selected from the group consisting of: a) prior myocardial infarction; b) prior stroke or prior transient ischaemic attack (TIA); c) prior coronary, carotid or peripheral arterial revascularisation; d) >50% stenosis on angiography or other imaging of coronary, carotid or lower extremity arteries; e) history of symptomatic coronary heart disease documented by positive exercise stress test or any cardiac imaging, or unstable angina pectoris with ECG (electrocardiogram) changes; f) asymptomatic cardiac ischemia | Type 1 diabetes Use of a GLP-1 receptor agonist (exenatide, liraglutide or other) or pramlintide or any dipeptidyl peptidase 4 (DPP-4) inhibitor within the 3 months prior to screening (trial start) Use of insulin other than human neutral protamine hagedorn (NPH) insulin or long-acting insulin analogue or premixed insulin within 3 months prior to screening. Short-term use of other insulin during this period in connection with intercurrent illness was allowed, at Investigator's discretion Acute decompensation of glycaemic control requiring immediate intensification of treatment to prevent acute complications of diabetes (e.g., diabetic ketoacidosis) in the previous 3 |

TABLE 2-continued

Subject inclusion and exclusion criteria (all inclusion criteria were fulfilled for eligible subjects; one or more exclusion criteria were fulfilled for subjects to be excluded; however, 150 patients violated at least one inclusion or exclusion criteria)

| Inclusion Criteria | Exclusion Criteria |
| --- | --- |
| documented by positive nuclear imaging test or exercise test or dobutamine stress echo; g) chronic heart failure NYHA class II-III; and h) chronic renal failure, having clinically reached a stage corresponding to a glomerular filtration rate <60 mL/min/ 1.73 m$^2$ per Modification of Diet in Renal Disease (MDRD) or <60 mL/min per Cockroft-Gault formula; wherein "prior" refers to before initiation of liraglutide administration; OR age ≥60 years at screening and other specified risk factors of vascular disease selected from the group consisting of: a) microalbuminuria or proteinuria; b) hypertension and/or left ventricular hypertrophy by ECG or imaging; c) left ventricular systolic or diastolic dysfunction by imaging; and d) ankle/brachial index <0.9 HbA$_{1c}$ ≥7.0% at screening Anti-diabetic drug naive or treated with one or more oral anti-diabetic drugs (OADs) or treated with human NPH insulin or long-acting insulin analogue or premixed insulin, alone or in combination with OAD(s) | months An acute coronary or cerebrovascular event in the previous 14 days Current continuous renal replacement therapy End-stage liver disease Chronic heart failure NYHA IV A prior solid organ transplant or awaiting solid organ transplant Family or personal history of multiple endocrine neoplasia type 2 (MEN2) or familial medullary thyroid carcinoma (FMTC) Personal history of non-familial medullary thyroid carcinoma Malignant neoplasm requiring chemotherapy, surgery, radiation or palliative therapy in the previous 5 years. Subjects with intraepithelial squamous cell carcinoma of the skin (Bowen's disease) treated with topical 5-fluorouracil (5FU) and subjects with basal cell skin cancer are allowed to enter the trial |

TABLE 3a

Baseline characteristics

|  | Liraglutide | Placebo |
| --- | --- | --- |
| Number of subjects | 4668 | 4672 |
| Male sex, N (%) | 3011 (64.5) | 2992 (64.0) |
| Age, years | 64.2 | 64.4 |
| Diabetes duration, years | 12.8 | 12.9 |
| HbA$_{1c}$, % | 8.7 | 8.7 |
| BMI, kg/m$^2$ | 32.5 | 32.5 |
| Body weight, kg | 91.9 | 91.6 |
| Systolic blood pressure, mmHg | 135.9 | 135.9 |
| Diastolic blood pressure, mmHg | 77.2 | 77.0 |
| Heart failure*, N (%) | 832 (17.8) | 821 (17.6) |

Full analysis set; data are mean unless stated otherwise.
*Heart failure includes NYHA class I, II and III.
%: proportion of subjects.
BMI: body mass index.
HbA1c: glycosylated haemoglobin.
NYHA: New York Heart Association.

TABLE 3b

Cardiovascular risk profile at baseline

|  | Liraglutide | | Placebo | |
| --- | --- | --- | --- | --- |
|  | N | % | N | % |
| Number of subjects | 4668 | | 4672 | |
| Age ≥50 years and established CV disease | 3815 | 81.7 | 3749 | 80.2 |
| Prior myocardial infarction | 1464 | 31.4 | 1400 | 30.0 |
| Prior stroke or prior TIA | 730 | 15.6 | 777 | 16.6 |
| Prior arterial revascularisation | 1766 | 37.8 | 1719 | 36.8 |
| >50% stenosis on angiography | 1188 | 25.4 | 1191 | 25.5 |
| Documented history of symptomatic coronary heart disease | 412 | 8.8 | 406 | 8.7 |
| Documented asymptomatic cardiac ischaemia | 1241 | 26.6 | 1231 | 26.3 |

TABLE 3b-continued

Cardiovascular risk profile at baseline

|  | Liraglutide | | Placebo | |
| --- | --- | --- | --- | --- |
|  | N | % | N | % |
| Chronic heart failure NYHA II or III | 653 | 14.0 | 652 | 14.0 |
| Chronic kidney failure | 1185 | 25.4 | 1122 | 24.0 |
| Age ≥60 years and risk factors for CV disease | 853 | 18.3 | 923 | 19.8 |
| Microalbuminuria or proteinuria | 504 | 10.8 | 560 | 12.0 |
| Hypertension or left ventricular hypertrophy | 249 | 5.3 | 253 | 5.4 |
| Left ventricular systolic or diastolic dysfunction | 204 | 4.4 | 191 | 4.1 |
| Ankle/brachial index <0.9 | 126 | 2.7 | 134 | 2.9 |

Full analysis set.
*Chronic kidney failure was defined as having clinically reached a stage corresponding to eGFR <60 mL/min/1.73 m$^2$ per MDRD or <60 mL/min per Cockroft-Gault formula, reported at the discretion of the investigator.
%: proportion of subjects.
eGFR: estimated glomerular filtration rate.
MDRD: modification of diet in renal disease.
N: number of subjects.
NYHA: New York Heart Association.
TIA: transient ischaemic attack.

TABLE 3c

Renal function at baseline

|  | Liraglutide | | Placebo | |
| --- | --- | --- | --- | --- |
|  | N | % | N | % |
| Number of subjects | 4668 | 100.0 | 4672 | 100.0 |
| Normal renal function (eGFR ≥90) | 1620 | 34.7 | 1655 | 35.4 |
| Mild renal impairment (eGFR 60-89) | 1932 | 41.4 | 1975 | 42.3 |

TABLE 3c-continued

Renal function at baseline

|  | Liraglutide | | Placebo | |
|---|---|---|---|---|
|  | N | % | N | % |
| Moderate renal impairment (eGFR 30-59) | 999 | 21.4 | 935 | 20.0 |
| Severe renal impairment (eGFR <30) | 117 | 2.5 | 107 | 2.3 |

Full analysis set. eGFR (mL/min/1.73 m$^2$) as per MDRD formula.
%: proportion of subjects.
eGFR: estimated glomerular filtration rate;
MDRD: modification of diet in renal disease.
N: number of subjects.

TABLE 3d

Cardiovascular medication at baseline

|  | Liraglutide | | Placebo | |
|---|---|---|---|---|
|  | N | % | N | % |
| Number of subjects | 4668 | | 4672 | |
| Antihypertensive therapy | 4322 | 92.6 | 4299 | 92.0 |
| Beta blockers | 2649 | 56.7 | 2524 | 54.0 |
| Calcium channel blockers | 1531 | 32.8 | 1477 | 31.6 |
| ACE inhibitors and ARB | 3898 | 83.5 | 3833 | 82.0 |
| Others | 468 | 10.0 | 452 | 9.7 |
| Diuretics | 1950 | 41.8 | 1949 | 41.7 |
| Loop diuretics | 823 | 17.6 | 833 | 17.8 |
| Others | 1405 | 30.1 | 1392 | 29.8 |
| Lipid-lowering drugs | 3554 | 76.1 | 3511 | 75.1 |
| Statins | 3395 | 72.7 | 3334 | 71.4 |
| Others | 655 | 14.0 | 676 | 14.5 |

TABLE 3d-continued

Cardiovascular medication at baseline

|  | Liraglutide | | Placebo | |
|---|---|---|---|---|
|  | N | % | N | % |
| Platelet aggregation inhibitors | 3203 | 68.6 | 3119 | 66.8 |
| Acetylsalicylic acid | 2975 | 63.7 | 2899 | 62.1 |
| Others | 718 | 15.4 | 743 | 15.9 |
| Other anti-thrombotic medication | 309 | 6.6 | 314 | 6.7 |

Full analysis set. 83 subjects had missing initiation drug date, these were assumed to be on treatment at baseline.
%: proportion of subjects.
ACE: angiotensin converting enzyme.
ARB: angiotensin receptor blocker.
N: number of subjects.

TABLE 3e

Antidiabetic treatment regimens at baseline

|  | Liraglutide | | Placebo | |
|---|---|---|---|---|
|  | N | % | N | % |
| Number of subjects | 4668 | | 4672 | |
| Insulin-naïve | 2633 | 56.4 | 2548 | 54.5 |
| Not on treatment* | 196 | 4.2 | 170 | 3.6 |
| OADs only | 2437 | 52.2 | 2378 | 50.9 |
| Insulin treatment | 2035 | 43.6 | 2124 | 45.5 |
| Insulin only | 361 | 7.7 | 376 | 8.0 |
| Insulin + OADs | 1674 | 35.9 | 1748 | 37.4 |

Full analysis set.
*Includes subjects not on insulin/OAD and subjects on no pharmacologic treatment.
%: proportion of subjects.
N: number of subjects.
OAD: oral antidiabetic drug.

TABLE 4

Standard of care guidelines for subjects in this trial

| Parameter | Standard of care guideline |
|---|---|
| Blood glucose | HbA1c ≤7.0% (individualized depending on patient). If >7.0%, additional HbA1c measurement after 3 m. If HbA1c still >7.0%, treatment was intensified to achieve target if appropriate. |
| Therapy | Lifestyle modifications and metformin are considered foundational therapy in most countries of this trial |
| Intensification | Add-on therapy: thiazolidinediones, sulfonylureas, a-glucosidase inhibitors, according to local labels (dipeptidyl peptidase-4 inhibitors and other incretin based therapies were not allowed). Insulin therapy should be based on local practice, including basal, basal/bolus, premix, and mealtime bolus (SIT). |
| Blood pressure | Target: 130/80 mmHg. |
| Antihypertensive therapy | First line: ACE inhibitors or ARBs. Based on individual patient needs: Ca$^{2+}$-blockers, diuretics, others. |
| Lipid targets and therapy | LDL <100 mg/dL (<70 mg/dL in patients with previous cardiovascular events). Statins recommended for all patients. Second line therapy at investigator discretion. |
| Antiplatelet therapy | Aspirin or clopidogrel (if aspirin intolerant) for patients with prior cardiovascular events (MI, cerebrovascular accident, or revascularization). |

Results: Cardiovascular Effects of Liraglutide

Figure 2:
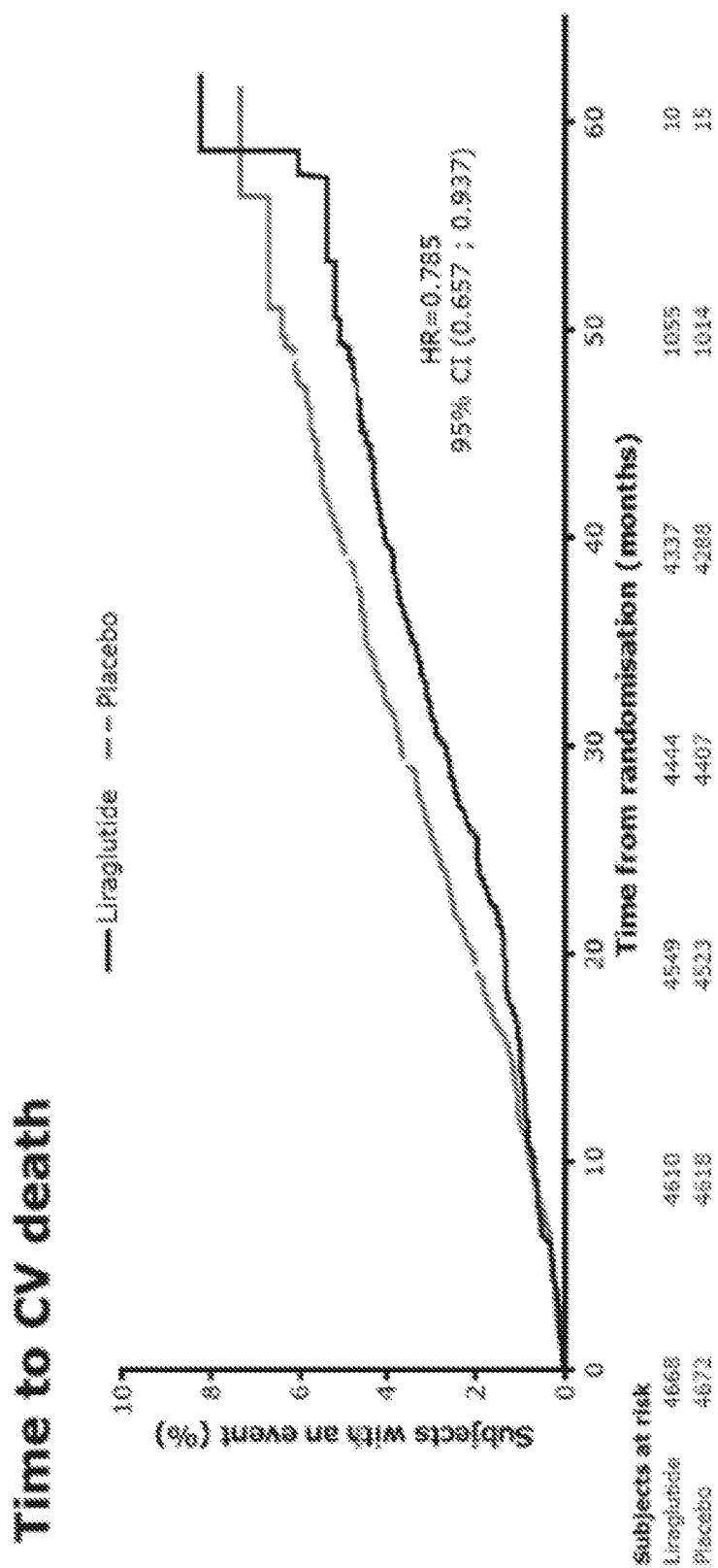
FIG. 2 shows time to CV death following administration of liraglutide or its placebo.
Figure 3:
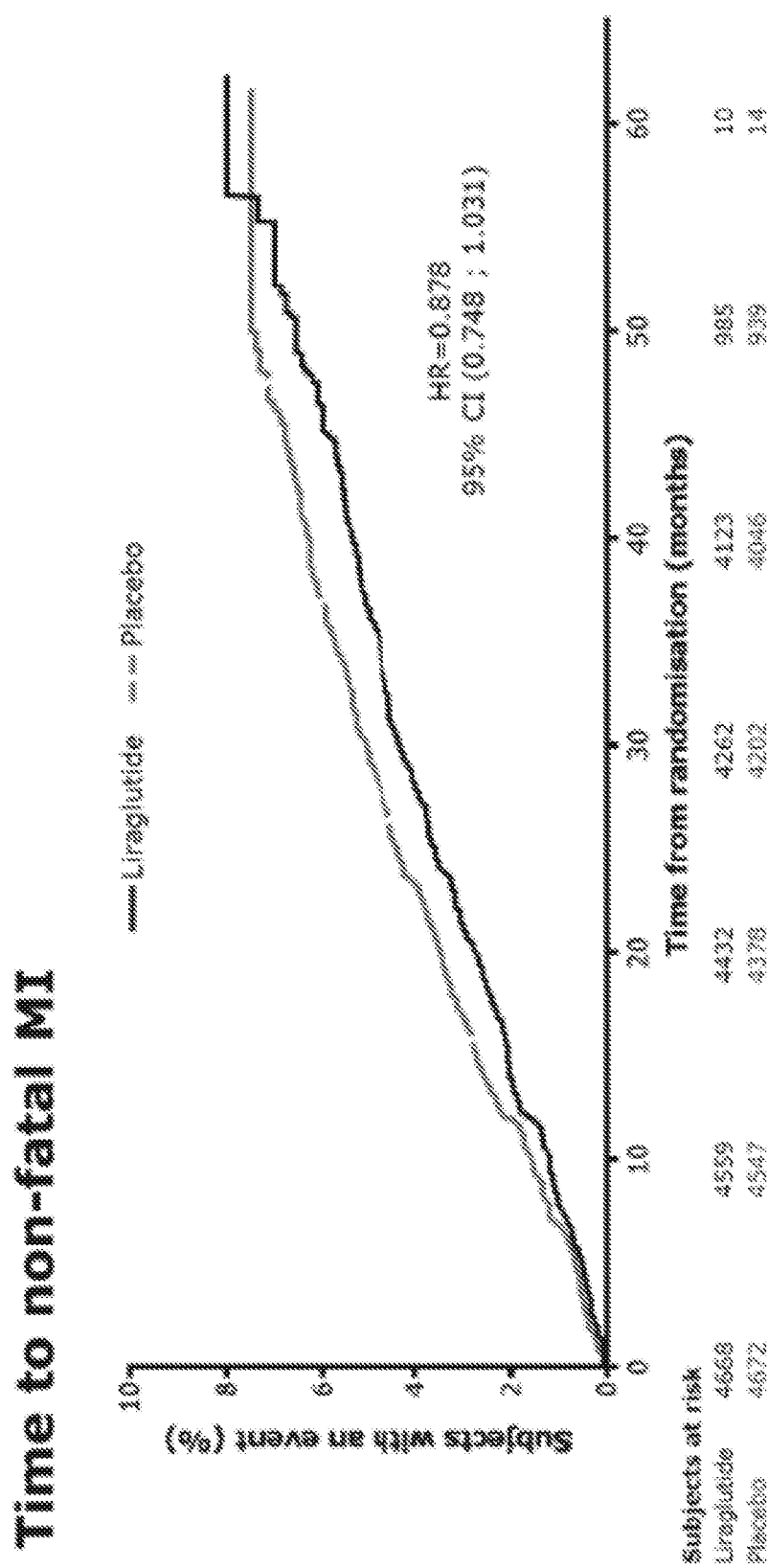
FIG. 3 shows time to first non-fatal MI following administration of liraglutide or its placebo.
Figure 4:
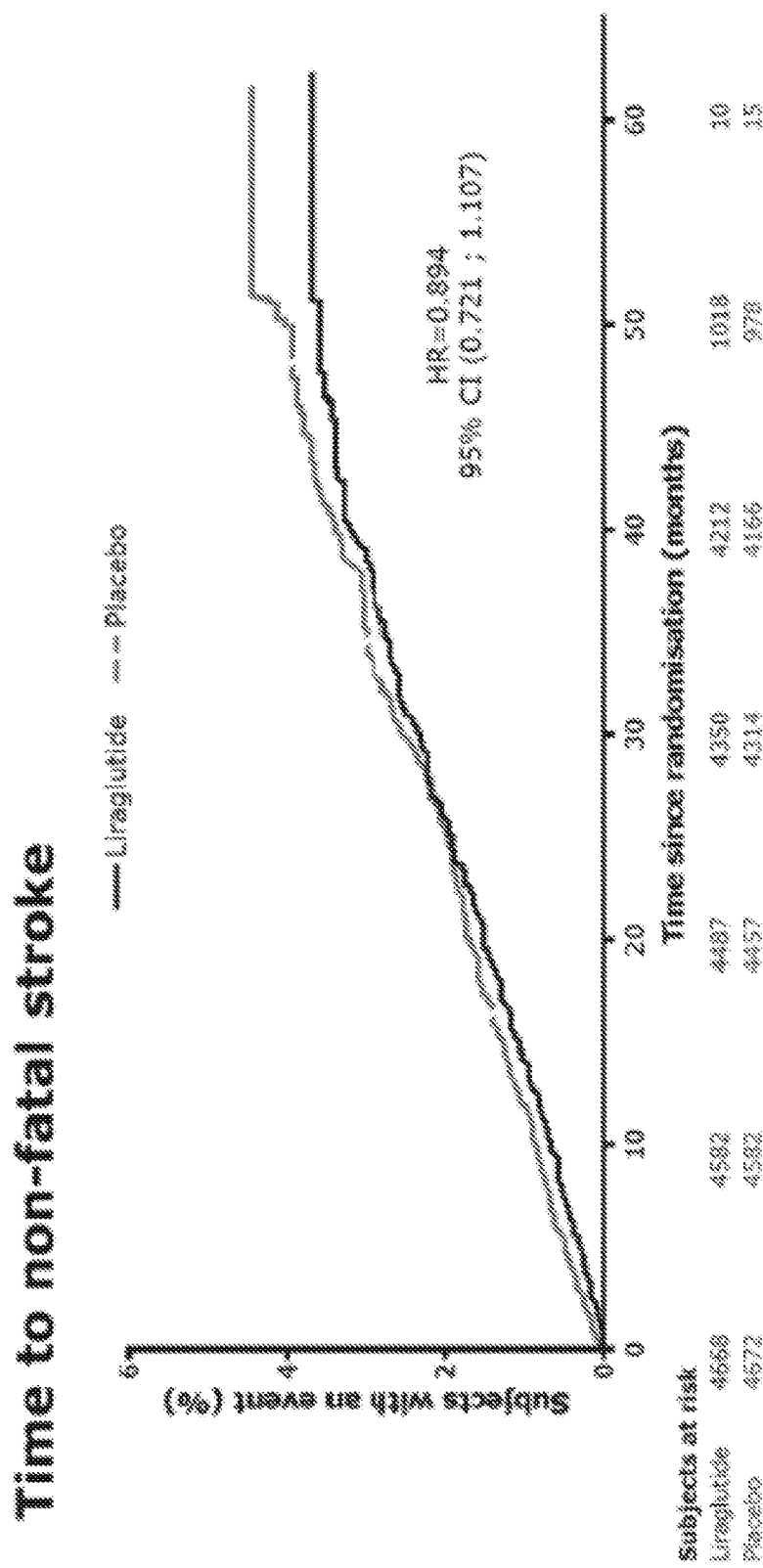
FIG. 4 shows time to first non-fatal stroke following administration of liraglutide or its placebo.
Figure 5:
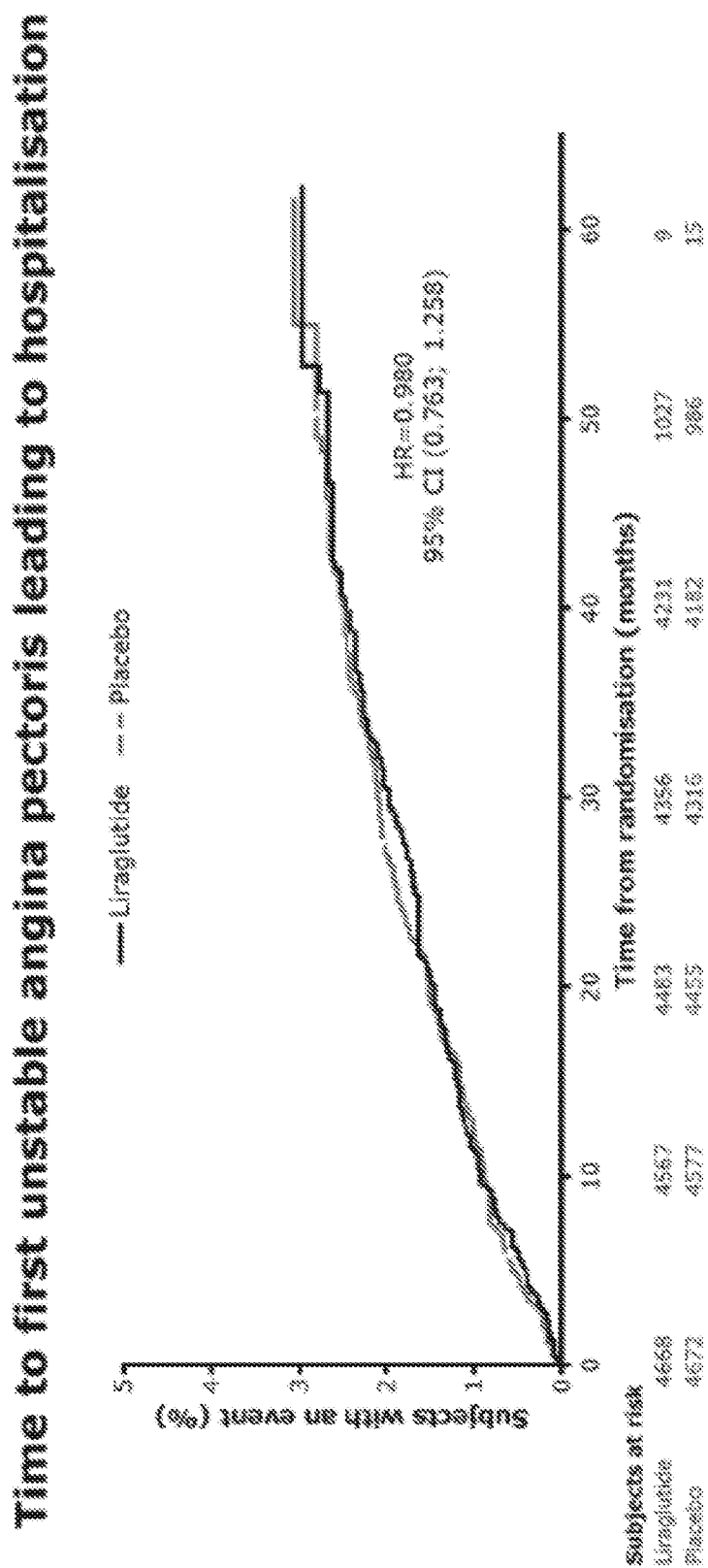
FIG. 5 shows time to first hospitalisation for unstable angina pectoris following administration of liraglutide or its placebo.
Figure 6:
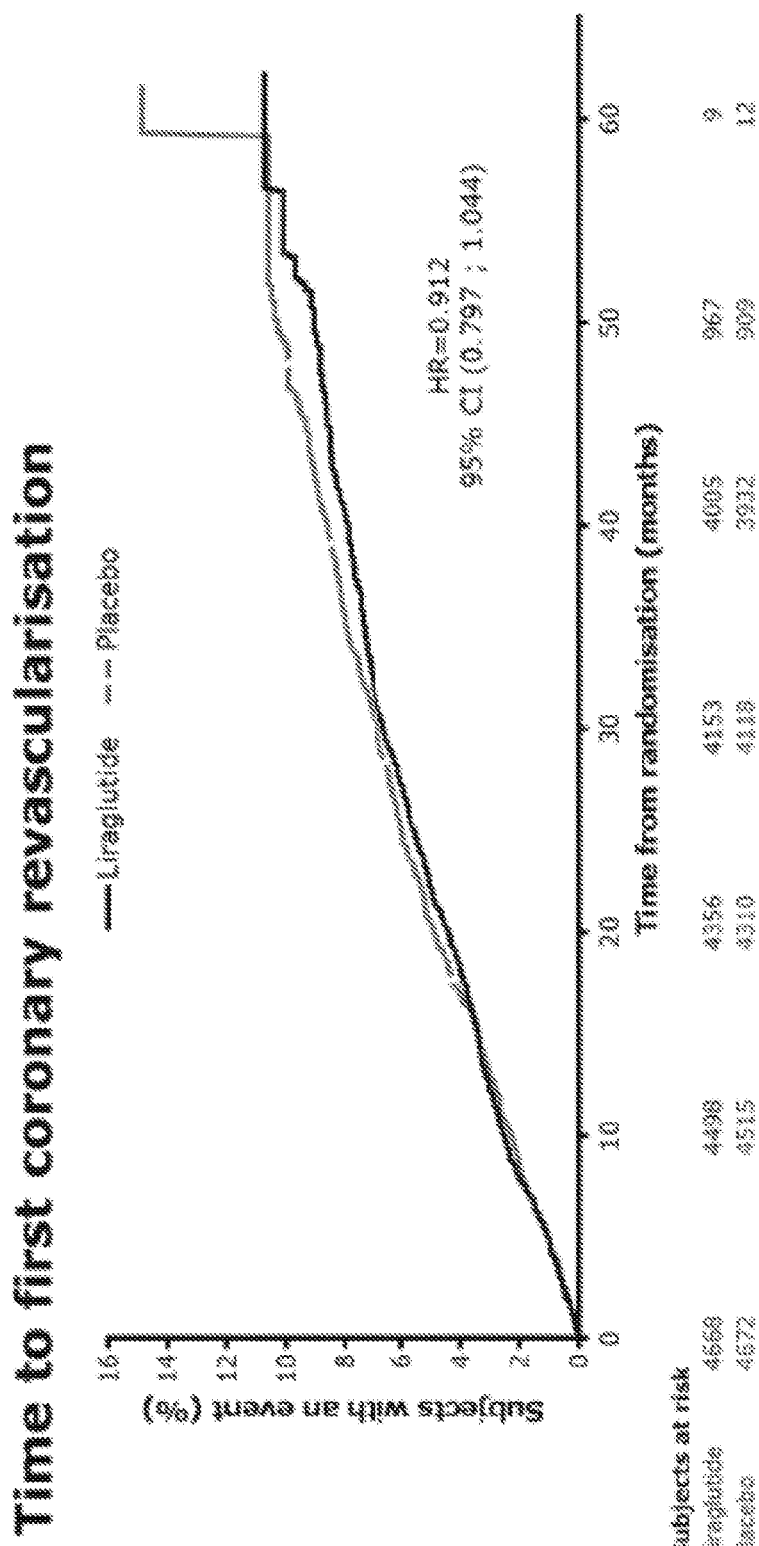
FIG. 6 shows time to first coronary revascularisation following administration of liraglutide or its placebo.
Figure 7:
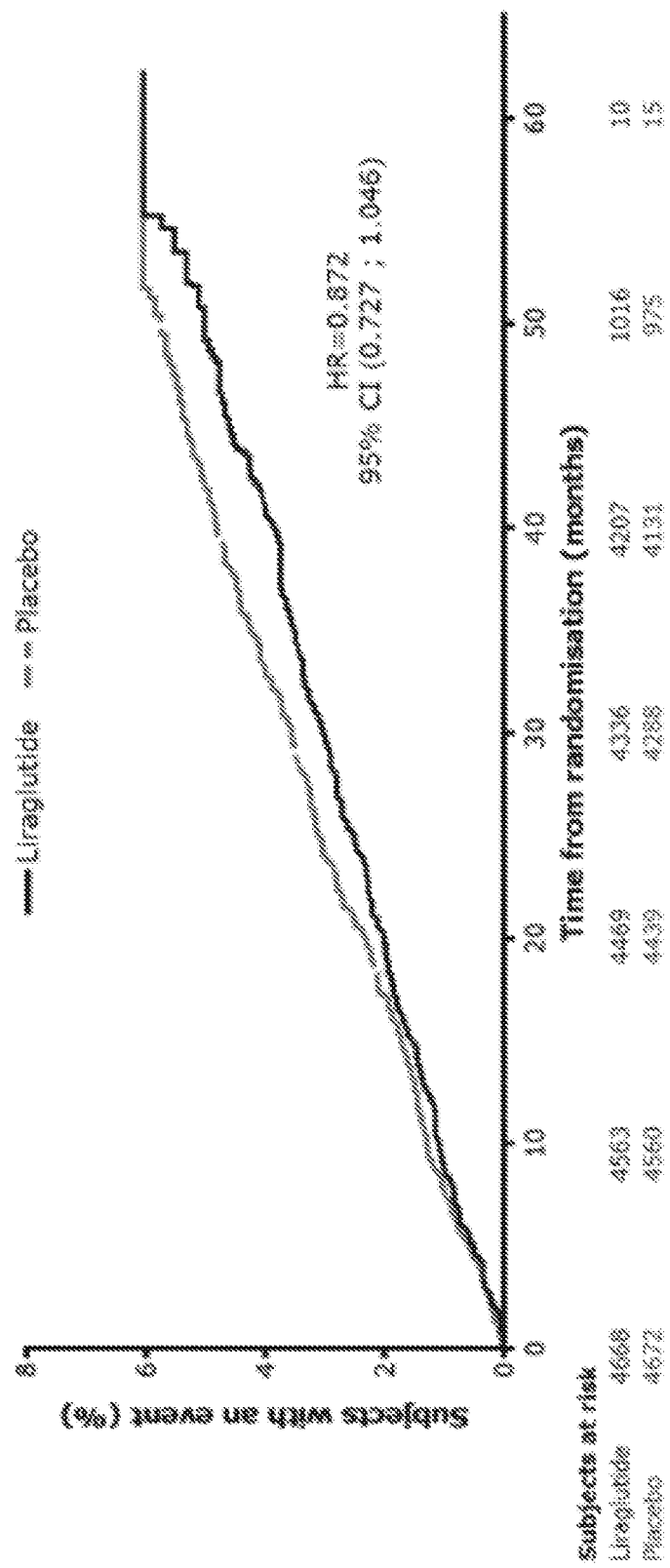
FIG. 7 shows time to first hospitalisation for heart failure following administration of liraglutide or its placebo.

Cardiovascular results from this trial are shown in Tables 5-11 and FIG. 1-7.

TABLE 5

First MACE selected from the group consisting of cardiovascular death, non-fatal MI, and non-fatal stroke as well as its composition

|  | Hazard ratio (95% CI) | Liraglutide N | % | Placebo N | % |
|---|---|---|---|---|---|
| Number of subjects (FAS) |  | 4668 |  | 4672 |  |
| First MACE* | 0.87 (0.78; 0.97) [p = 0.006 for superiority] | 607 | 13.0 | 692 | 14.8 |
| CV death |  | 180 |  | 225 |  |
| Non-fatal MI |  | 275 |  | 304 |  |
| Non-fatal stroke |  | 152 |  | 163 |  |

One-sided test for HR.
Cox proportional hazard model adjusted for treatment. Analysis includes subjects with a first MACE, as defined, between randomisation date and follow-up date; subjects without an event are censored at time of last contact (phone or visit); events which occur before randomisation are not used for defining first event.
*In this table MACE is selected from the group consisting of cardiovascular death, non-fatal stroke, and non-fatal MI. Full analysis set (FAS).
%: proportion of subjects.

TABLE 6

First MACE selected from the group consisting of cardiovascular death, non-fatal stroke, non-fatal myocardial infarction, hospitalisation for unstable angina pectoris, coronary revascularisation, and hospitalisation for heart failure as well as its composition

|  | Hazard ratio (95% CI) | Liraglutide N | % | Placebo N | % |
|---|---|---|---|---|---|
| Number of subjects (FAS) |  | 4668 | 100 | 4672 | 100 |
| First MACE* | 0.88 (0.81; 0.96) | 947 | 20.3 | 1061 | 22.7 |
| Components of first MACE* |  |  |  |  |  |
| Cardiovascular death |  | 141 |  | 182 |  |
| Non-fatal stroke |  | 238 |  | 257 |  |
| Non-fatal MI |  | 140 |  | 152 |  |
| Hospitalisation for UAP |  | 104 |  | 96 |  |
| Coronary revascularisation |  | 162 |  | 190 |  |
| Hospitalisation for heart failure |  | 162 |  | 184 |  |

One-sided test for HR. Cox proportional hazard model adjusted for treatment. Analysis includes subjects with a first MACE, as defined, between randomisation date and follow-up date; subjects without an event are censored at time of last contact (phone or visit); events which occur before randomisation are not used for defining first event.
*In this table MACE is selected from the group consisting of cardiovascular death, non-fatal stroke, non-fatal MI, hospitalisation for UAP, coronary revascularisation, and hospitalisation for heart failure. Full analysis set (FAS).
%: proportion of subjects.

TABLE 7

MACE selected from the group consisting of cardiovascular death, non-fatal stroke, non-fatal myocardial infarction, hospitalisation for unstable angina pectoris, coronary revascularisation, and hospitalisation for heart failure as well as time to first event in each listed member of this group

|  | Hazard ratio (95% CI) | Liraglutide N | % | Placebo N | % |
|---|---|---|---|---|---|
| Number of subjects (FAS) |  | 4668 | 100 | 4672 | 100 |
| First MACE* | 0.88 (0.81; 0.96) | 947 | 20.3 | 1061 | 22.7 |
| Individual components of total MACE* |  |  |  |  |  |
| Cardiovascular death | 0.78 (0.66; 0.94) | 218 | 4.7 | 276 | 5.9 |
| Non-fatal stroke | 0.89 (0.72; 1.11) | 159 | 3.4 | 177 | 3.8 |
| Non-fatal MI | 0.88 (0.75; 1.03) | 281 | 6.0 | 317 | 6.8 |
| Hospitalisation for UAP | 0.98 (0.76; 1.26) | 122 | 2.6 | 124 | 2.7 |
| Coronary revascularisation | 0.91 (0.80; 1.04) | 405 | 8.7 | 441 | 9.4 |
| Hospitalisation for heart failure | 0.87 (0.73; 1.05) | 218 | 4.7 | 248 | 5.3 |

Full analysis set (FAS). Cox proportional hazard model adjusted for treatment
*In this table MACE is selected from the group consisting of cardiovascular death, non-fatal stroke, non-fatal MI, hospitalisation for UAP, coronary revascularisation, and hospitalisation for heart failure.
%: proportion of subjects.
N: number of subjects.

TABLE 8

Time to first MACE selected from the group consisting of cardiovascular death, non-fatal MI, and non-fatal stroke and subgroups hereof

| Factor | N | % | Hazard ratio (95% CI) |
|---|---|---|---|
| First MACE* | 9340 | 13.9 | 0.87 (0.78; 0.97) |
| Sex |  |  |  |
| Female | 3337 | 11.7 | 0.88 (0.72; 1.08) |
| Male | 6003 | 15.1 | 0.86 (0.76; 0.98) |
| Age |  |  |  |
| Adults (<60 years) | 2321 | 13.2 | 0.78 (0.62; 0.97) |
| Elderly (≥60 years) | 7019 | 14.1 | 0.90 (0.80; 1.02) |
| Region |  |  |  |
| Europe | 3631 | 13.3 | 0.82 (0.69**; 0.98) |
| North America | 2847 | 15.0 | 1.01 (0.84; 1.22) |
| Asia | 711 | 8.6 | 0.62 (0.37; 1.04) |
| Rest of the world | 2151 | 15.2 | 0.83 (0.67**; 1.03) |
| Race |  |  |  |
| White | 7238 | 14.3 | 0.91 (0.80; 1.02) |
| Black or African American | 777 | 13.6 | 0.87 (0.59; 1.27) |
| Asian | 936 | 10.3 | 0.70 (0.46; 1.04) |
| Other | 389 | 16.2 | 0.61 (0.37; 1.00) |
| Ethnicity |  |  |  |
| Hispanic or Latino | 1134 | 13.6 | 0.74 (0.54; 1.02) |
| Not Hispanic or Latino | 8206 | 14.0 | 0.89 (0.79; 1.00) |
| BMI |  |  |  |
| ≤30 kg/m$^2$ | 3574 | 14.0 | 0.96 (0.81; 1.15) |
| >30 kg/m$^2$ | 5757 | 13.8 | 0.82 (0.71; 0.94) |
| HbA$_{1c}$ |  |  |  |
| ≤8.3% | 4768 | 13.0 | 0.90 (0.77; 1.05) |
| >8.3% | 4571 | 14.9 | 0.84 (0.72; 0.98) |
| Diabetes duration |  |  |  |
| ≤11 years | 4429 | 13.1 | 0.82 (0.70; 0.97) |
| >11 years | 4892 | 14.6 | 0.91 (0.78; 1.05) |
| Cardiovascular risk |  |  |  |
| Age ≥50 years and established CV disease | 7564 | 15.3 | 0.83 (0.74; 0.96)*** |
| Age ≥60 years and risk factors for CV disease | 1776 | 7.9 | 1.18 (0.84; 1.64)**** |

TABLE 8-continued

Time to first MACE selected from the group consisting of cardiovascular death, non-fatal MI, and non-fatal stroke and subgroups hereof

| Factor | N | % | Hazard ratio (95% CI) |
|---|---|---|---|
| Chronic heart failure | | | |
| Yes | 1305 | 17.7 | 0.94 (0.72; 1.21) |
| No | 8035 | 13.3 | 0.86 (0.76; 0.96) |
| Antidiabetic therapy* | | | |
| 1 OAD | 1820 | 12.3 | 0.75 (0.58; 0.98) |
| >1 OAD | 2995 | 12.9 | 0.96 (0.79; 1.17) |
| Insulin and ≥1 OAD | 3419 | 14.1 | 0.88 (0.74; 1.06) |
| Insulin, no OAD | 739 | 21.1 | 0.87 (0.63; 1.19) |
| None | 367 | 14.2 | 0.72 (0.42; 1.24) |
| eGFR-MDRD | | | |
| eGFR <60 | 1883 | 17.7 | 0.80 (0.64; 0.99) |
| eGFR ≥60 | 7262 | 12.7 | 0.90 (0.79; 1.02) |
| eGFR-MDRD | | | |
| eGFR <30 | 188 | 23.9 | 0.68 (0.37; 1.24) |
| eGFR ≥30 | 9145 | 13.7 | 0.88 (0.79; 0.98) |
| eGFR-CKD-EPI | | | |
| eGFR <60 | 1719 | 18.9 | 0.75 (0.60; 0.93) |
| eGFR ≥60 | 7422 | 12.5 | 0.90 (0.80; 1.03) |
| eGFR-CKD-EPI | | | |
| eGFR <30 | 192 | 22.4 | 0.85 (0.46; 1.55) |
| eGFR ≥30 | 9141 | 13.7 | 0.87 (0.78; 0.97) |

Cox proportional hazard model adjusted for treatment. No adjustment for multiple testing.
*In this table MACE is selected from the group consisting of cardiovascular death, non-fatal stroke, and non-fatal MI.
%: proportion of subjects with a first MACE, as defined, between randomisation date and follow-up date.
N: number of subjects.
**Updated result for lower end point of 95% CI is 0.68.
***Updated result is 0.85 (0.74; 0.97).
****Updated result is 1.19 (0.85; 1.67).

TABLE 9

Time to first MACE selected from the group consisting of cardiovascular death, non-fatal MI, and non-fatal stroke and additional subgroups hereof

| Factor | Hazard ratio (95% CI) |
|---|---|
| First MACE* | 0.87 (0.78; 0.97) |
| Subject profile at baseline | |
| Subjects with established vascular disease and ≥60 years of age | 0.85 (0.75; 0.98) |
| Subjects with risk factors of vascular disease and ≥60 years of age | 1.18 (0.84; 1.64) |
| HbA$_{1c}$ | |
| <9.0% | 0.89 (0.78; 1.03) |
| ≥9.0% | 0.83 (0.69; 0.98) |
| HbA$_{1c}$ | |
| <8.4% | 0.90 (0.77; 1.05) |
| ≥8.4% | 0.84 (0.72; 0.98) |
| HbA$_{1c}$ | |
| <10.8% | 0.87 (0.77; 0.98) |
| ≥10.8% | 0.85 (0.63; 1.13) |
| eGFR-MDRD | |
| eGFR <30 | 0.86 (0.49; 1.50) |
| eGFR ≥30 to ≤59 | 0.69 (0.55; 0.86) |
| eGFR >59 | 0.94 (0.82; 1.06) |
| eGFR-MDRD | |
| eGFR <40 | 0.68 (0.48; 0.96)** |
| eGFR ≥40 to <50 | 0.87 (0.62; 1.23)*** |
| eGFR ≥50 | 0.89 (0.78; 1.00)**** |

TABLE 9-continued

Time to first MACE selected from the group consisting of cardiovascular death, non-fatal MI, and non-fatal stroke and additional subgroups hereof

| Factor | Hazard ratio (95% CI) |
|---|---|
| BMI | |
| <30.4 kg/m$^2$ | 0.95 (0.80; 1.13) |
| ≥30.4 kg/m$^2$ | 0.82 (0.71; 0.94) |
| BMI | |
| <33.0 kg/m$^2$ | 0.88 (0.76; 1.01) |
| ≥33.0 kg/m$^2$ | 0.86 (0.72; 1.02) |

Cox proportional hazard model adjusted for treatment. No adjustment for multiple testing.
*In this table MACE is selected from the group consisting of cardiovascular death, non-fatal stroke, and non-fatal MI.
**Updated result is 0.64 (0.45; 0.92).
***Updated result is 0.87 (0.61; 1.25).
****Updated result is 0.89 (0.79; 1.01).

TABLE 10

Time to all-cause death, CV death, and non-CV death

| | Hazard ratio | Liraglutide | | Placebo | |
|---|---|---|---|---|---|
| | (95% CI) | N | % | N | % |
| Number of subjects | | 4668 | 100.0 | 4672 | 100.0 |
| All-cause death | 0.85 (0.74; 0.97) | 379 | 8.1 | 445 | 9.5 |
| CV death | 0.78 (0.66; 0.94) | 218 | 4.7 | 276 | 5.9 |
| Non-CV death | 0.95 (0.76; 1.17) | 161 | 3.5 | 169 | 3.6 |

Full analysis set. Time to all-cause death, CV death, and non-CV death. Cox proportional hazard model adjusted for treatment. Analysis includes events between randomisation date and follow-up date. Subjects without an event were censored at the time of last contact (phone or visit).
%: proportion of subjects.
N: number of subjects.

TABLE 11

Time to CV death excluding death from unknown cause (i.e. only death clinically documented to occur from CV cause)

| | Hazard ratio (95% CI) |
|---|---|
| CV death excluding death from unknown cause | 0.75 (0.61; 0.93) |

Full analysis set. Time to CV death excluding death from unknown cause. Cox proportional hazard model adjusted for treatment. Analysis includes events between randomisation date and follow-up date. Subjects without an event were censored at the time of last contact (phone or visit).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for reducing the development of a major adverse cardiovascular event (MACE), comprising administering liraglutide in a therapeutically effective amount to a subject in need thereof,
   wherein the subject has type 2 diabetes and cardiovascular disease,
   wherein the subject is not administered a dipeptidyl peptidase-4 inhibitor, and
   wherein the MACE is selected from the group consisting of cardiovascular death, non-fatal myocardial infarction, and non-fatal stroke.

2. The method according to claim 1, wherein the subject is being administered cardiovascular medication.

3. The method according to claim 1, wherein the subject is ≥50 years of age.

4. The method according to claim 1, wherein the liraglutide is in an amount selected from 0.6 mg, 1.2 mg, and 1.8 mg.

5. The method according to claim 1, wherein the subject is ≥50 years of age, and wherein the liraglutide is in an amount selected from 0.6 mg, 1.2 mg, and 1.8 mg.

6. A method for reducing the development of a major adverse cardiovascular event (MACE), comprising administering a pharmaceutical composition to a subject in need thereof,
 wherein the subject has type 2 diabetes and cardiovascular disease,
 wherein the pharmaceutical composition consists essentially of liraglutide in a therapeutically effective amount and one or more excipients, and
 wherein the MACE is selected from the group consisting of cardiovascular death, non-fatal myocardial infarction, and non-fatal stroke.

7. The method according to claim 6, wherein the subject is ≥50 years of age.

8. The method according to claim 6, wherein the liraglutide is administered in an amount selected from 0.6 mg, 1.2 mg, and 1.8 mg.

9. The method according to claim 6, wherein the subject is ≥50 years of age, and wherein the liraglutide is in an amount selected from 0.6 mg, 1.2 mg, and 1.8 mg.

10. The method according to claim 6, wherein the one or more excipients is selected from the group consisting of a buffer system, preservative, tonicity agent, chelating agent, stabilizer, and surfactant.

11. The method according to claim 6, wherein the pharmaceutical composition consists of about 6 mg/ml liraglutide, about 2-15 mM phosphate buffer, about 2-25 mg/ml propylene glycol, about 1-18 mg/ml phenol, and a pH in the range of 7.5-9.0.

12. The method according to claim 11, wherein the pharmaceutical composition consists of 6 mg/ml liraglutide, 1.42 mg/ml disodium phosphate dihydrate, 14.0 mg/ml propylene glycol, 5.5 mg/ml phenol, and a pH of 8.15.

13. A method for reducing the development of a major adverse cardiovascular event (MACE), comprising administering a pharmaceutical composition to a subject in need thereof,
 wherein the subject has type 2 diabetes and cardiovascular disease,
 wherein the pharmaceutical composition comprises liraglutide in a therapeutically effective amount and as the only active therapeutic ingredient, and
 wherein the MACE is selected from the group consisting of cardiovascular death, non-fatal myocardial infarction, and non-fatal stroke.

14. The method according to claim 13, wherein the subject is ≥50 years of age.

15. The method according to claim 13, wherein the liraglutide is administered in an amount selected from 0.6 mg, 1.2 mg, and 1.8 mg.

16. The method according to claim 13, wherein the subject is ≥50 years of age, and wherein the liraglutide is in an amount selected from 0.6 mg, 1.2 mg, and 1.8 mg.

17. The method according to claim 13, wherein the concentration of liraglutide is about 6 mg/ml, and wherein the pharmaceutical composition further comprises about 2-15 mM phosphate buffer, about 2-25 mg/ml propylene glycol, about 1-18 mg/ml phenol, and a pH in the range of 7.5-9.0.

18. The method according to claim 13, wherein the concentration of liraglutide is 6 mg/ml, and wherein the pharmaceutical composition further comprises 1.42 mg/ml disodium phosphate dihydrate, 14.0 mg/ml propylene glycol, 5.5 mg/ml phenol, and a pH of 8.15.

\* \* \* \* \*